United States Patent
Anderson et al.

(10) Patent No.: US 9,707,036 B2
(45) Date of Patent: Jul. 18, 2017

(54) DEVICES AND METHODS FOR NERVE MODULATION USING LOCALIZED INDIFFERENT ELECTRODES

(71) Applicant: Boston Scientific Scimed, Inc., Maple Grove, MN (US)

(72) Inventors: James M. Anderson, Corcoran, MN (US); Derek C. Sutermeister, Ham Lake, MN (US); Huisun Wang, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 268 days.

(21) Appl. No.: 14/314,734

(22) Filed: Jun. 25, 2014

(65) Prior Publication Data

US 2014/0378962 A1 Dec. 25, 2014

Related U.S. Application Data

(60) Provisional application No. 61/839,243, filed on Jun. 25, 2013.

(51) Int. Cl.
*A61B 18/14* (2006.01)
*A61B 18/16* (2006.01)
*A61B 18/00* (2006.01)

(52) U.S. Cl.
CPC .......... *A61B 18/16* (2013.01); *A61B 18/1492* (2013.01); *A61B 2018/0022* (2013.01);
(Continued)

(58) Field of Classification Search
CPC ........ A61B 2018/162; A61B 2018/165; A61B 2018/00577; A61B 2018/00505;
(Continued)

(56) References Cited

U.S. PATENT DOCUMENTS

| 164,184 A | 6/1875 | Kiddee |
| 852,787 A | 5/1907 | Hoerner |

(Continued)

FOREIGN PATENT DOCUMENTS

| DE | 10038737 A1 | 2/2002 |
| EP | 1053720 A1 | 11/2000 |

(Continued)

OTHER PUBLICATIONS

US 8,398,630, 03/2013, Demarais et al. (withdrawn)
(Continued)

*Primary Examiner* — Jaymi Della

(57) ABSTRACT

The disclosure pertains to an intravascular catheter for nerve modulation. The catheter includes an elongate member having a proximal end and a distal end, and an inflatable balloon secured adjacent to the distal end of the elongate member. The balloon includes an exterior surface and an interior surface defining a lumen. The lumen includes a section that is permeable to radiofrequency (RF) radiation. The section extends from the interior surface of the balloon to the exterior surface of the balloon. A first electrode is disposed within the inflatable balloon and indifferent electrodes are disposed external to the inflatable balloon.

4 Claims, 5 Drawing Sheets

(52) U.S. Cl.
CPC .............. *A61B 2018/00267* (2013.01); *A61B 2018/00404* (2013.01); *A61B 2018/00434* (2013.01); *A61B 2018/00511* (2013.01); *A61B 2018/00577* (2013.01); *A61B 2018/1467* (2013.01); *A61B 2018/162* (2013.01); *A61B 2018/165* (2013.01)

(58) Field of Classification Search
CPC .. A61B 2018/00511; A61B 2018/0022; A61B 2018/00434; A61B 2018/00255; A61B 2018/0025; A61B 2018/00261
See application file for complete search history.

(56) References Cited

U.S. PATENT DOCUMENTS

| | | | |
|---|---|---|---|
| 921,973 | A | 5/1909 | Gillett et al. |
| 976,733 | A | 11/1910 | Gilliland |
| 1,167,014 | A | 1/1916 | O'Brien |
| 2,505,358 | A | 4/1950 | Gusberg et al. |
| 2,701,559 | A | 2/1955 | Cooper |
| 3,108,593 | A | 10/1963 | Glassman |
| 3,108,594 | A | 10/1963 | Glassman |
| 3,540,431 | A | 11/1970 | Mobin |
| 3,952,747 | A | 4/1976 | Kimmell |
| 3,996,938 | A | 12/1976 | Clark, III |
| 4,046,150 | A | 9/1977 | Schwartz et al. |
| 4,290,427 | A | 9/1981 | Chin |
| 4,402,686 | A | 9/1983 | Medel |
| 4,483,341 | A | 11/1984 | Witteles et al. |
| 4,531,943 | A | 7/1985 | Van Tassel et al. |
| 4,574,804 | A | 3/1986 | Kurwa |
| 4,587,975 | A | 5/1986 | Salo et al. |
| 4,649,936 | A | 3/1987 | Ungar et al. |
| 4,682,596 | A | 7/1987 | Bales et al. |
| 4,709,698 | A | 12/1987 | Johnston et al. |
| 4,765,331 | A | 8/1988 | Petruzzi et al. |
| 4,770,653 | A | 9/1988 | Shturman |
| 4,784,132 | A | 11/1988 | Fox et al. |
| 4,784,162 | A | 11/1988 | Ricks et al. |
| 4,785,806 | A | 11/1988 | Deckelbaum et al. |
| 4,788,975 | A | 12/1988 | Shturman et al. |
| 4,790,310 | A | 12/1988 | Ginsburg et al. |
| 4,799,479 | A | 1/1989 | Spears |
| 4,823,791 | A | 4/1989 | D'Amelio et al. |
| 4,830,003 | A | 5/1989 | Wolff et al. |
| 4,849,484 | A | 7/1989 | Heard |
| 4,862,886 | A | 9/1989 | Clarke et al. |
| 4,887,605 | A | 12/1989 | Angelsen et al. |
| 4,890,623 | A | 1/1990 | Cook et al. |
| 4,920,979 | A | 5/1990 | Bullara et al. |
| 4,938,766 | A | 7/1990 | Jarvik |
| 4,955,377 | A | 9/1990 | Lennox et al. |
| 4,976,711 | A | 12/1990 | Parins et al. |
| 5,003,991 | A * | 4/1991 | Takayama ............... A61N 1/40 607/116 |
| 5,034,010 | A | 7/1991 | Kittrell et al. |
| 5,052,402 | A | 10/1991 | Bencini et al. |
| 5,053,033 | A | 10/1991 | Clarke et al. |
| 5,071,424 | A | 12/1991 | Reger et al. |
| 5,074,871 | A | 12/1991 | Groshong et al. |
| 5,098,429 | A | 3/1992 | Sterzer et al. |
| 5,098,431 | A | 3/1992 | Rydell |
| 5,109,859 | A | 5/1992 | Jenkins |
| 5,125,928 | A | 6/1992 | Parins et al. |
| 5,129,396 | A | 7/1992 | Rosen et al. |
| 5,139,496 | A | 8/1992 | Hed |
| 5,143,836 | A | 9/1992 | Hartman et al. |
| 5,151,100 | A * | 9/1992 | Abele ............... A61B 18/082 606/28 |
| 5,156,610 | A | 10/1992 | Reger et al. |
| 5,158,564 | A | 10/1992 | Schnepp-Pesch |
| 5,170,802 | A | 12/1992 | Mehra |
| 5,178,620 | A | 1/1993 | Eggers et al. |
| 5,178,625 | A | 1/1993 | Groshong et al. |
| 5,190,540 | A | 3/1993 | Lee |
| 5,211,651 | A | 5/1993 | Reger et al. |
| 5,234,407 | A | 8/1993 | Teirstein et al. |
| 5,242,441 | A | 9/1993 | Avitall |
| 5,251,634 | A | 10/1993 | Weinberg et al. |
| 5,255,679 | A | 10/1993 | Imran |
| 5,263,493 | A | 11/1993 | Avitall |
| 5,267,954 | A | 12/1993 | Nita et al. |
| 5,277,201 | A | 1/1994 | Stern et al. |
| 5,282,484 | A | 2/1994 | Reger et al. |
| 5,286,254 | A | 2/1994 | Shapland et al. |
| 5,290,306 | A | 3/1994 | Trotta et al. |
| 5,295,484 | A | 3/1994 | Marcus |
| 5,297,564 | A | 3/1994 | Love et al. |
| 5,300,068 | A | 4/1994 | Rosar et al. |
| 5,301,683 | A | 4/1994 | Durkan |
| 5,304,115 | A | 4/1994 | Pflueger et al. |
| 5,304,121 | A | 4/1994 | Sahatjian |
| 5,304,171 | A | 4/1994 | Gregory et al. |
| 5,304,173 | A | 4/1994 | Kittrell et al. |
| 5,306,250 | A | 4/1994 | March et al. |
| 5,312,328 | A | 5/1994 | Nita et al. |
| 5,314,466 | A | 5/1994 | Stern et al. |
| 5,322,064 | A | 6/1994 | Lundquist |
| 5,324,255 | A | 6/1994 | Passafaro et al. |
| 5,326,341 | A | 7/1994 | Lew et al. |
| 5,326,342 | A | 7/1994 | Pflueger et al. |
| 5,330,518 | A | 7/1994 | Neilson et al. |
| 5,333,614 | A | 8/1994 | Feiring |
| 5,342,292 | A | 8/1994 | Nita et al. |
| 5,344,395 | A | 9/1994 | Whalen et al. |
| 5,364,392 | A | 11/1994 | Warner et al. |
| 5,365,172 | A | 11/1994 | Hrovat et al. |
| 5,368,557 | A | 11/1994 | Nita et al. |
| 5,368,558 | A | 11/1994 | Nita et al. |
| 5,380,274 | A | 1/1995 | Nita et al. |
| 5,380,319 | A | 1/1995 | Saito et al. |
| 5,382,228 | A | 1/1995 | Nita et al. |
| 5,383,874 | A | 1/1995 | Jackson et al. |
| 5,383,917 | A | 1/1995 | Desai et al. |
| 5,397,301 | A | 3/1995 | Pflueger et al. |
| 5,397,339 | A | 3/1995 | Desai |
| 5,401,272 | A | 3/1995 | Perkins et al. |
| 5,403,311 | A | 4/1995 | Abele et al. |
| 5,405,318 | A | 4/1995 | Nita et al. |
| 5,405,346 | A | 4/1995 | Grundy et al. |
| 5,409,000 | A | 4/1995 | Imran |
| 5,417,672 | A | 5/1995 | Nita et al. |
| 5,419,767 | A | 5/1995 | Eggers et al. |
| 5,427,118 | A | 6/1995 | Nita et al. |
| 5,432,876 | A | 7/1995 | Appeldorn et al. |
| 5,441,498 | A | 8/1995 | Perkins et al. |
| 5,447,509 | A | 9/1995 | Mills et al. |
| 5,451,207 | A | 9/1995 | Yock et al. |
| 5,453,091 | A | 9/1995 | Taylor et al. |
| 5,454,788 | A | 10/1995 | Walker et al. |
| 5,454,809 | A | 10/1995 | Janssen |
| 5,455,029 | A | 10/1995 | Hartman et al. |
| 5,456,682 | A | 10/1995 | Edwards et al. |
| 5,457,042 | A | 10/1995 | Hartman et al. |
| 5,471,982 | A | 12/1995 | Edwards et al. |
| 5,474,530 | A | 12/1995 | Passafaro et al. |
| 5,478,351 | A | 12/1995 | Meade et al. |
| 5,496,311 | A | 3/1996 | Abele et al. |
| 5,496,312 | A | 3/1996 | Klicek et al. |
| 5,498,261 | A | 3/1996 | Strul |
| 5,505,201 | A | 4/1996 | Grill et al. |
| 5,505,730 | A | 4/1996 | Edwards |
| 5,507,744 | A | 4/1996 | Tay et al. |
| 5,512,051 | A | 4/1996 | Wang et al. |
| 5,522,873 | A | 6/1996 | Jackman et al. |
| 5,531,520 | A | 7/1996 | Grimson et al. |
| 5,540,656 | A | 7/1996 | Pflueger et al. |
| 5,540,679 | A * | 7/1996 | Fram ............... A61B 18/082 606/27 |
| 5,540,681 | A | 7/1996 | Strul et al. |
| 5,542,917 | A | 8/1996 | Nita et al. |
| 5,545,161 | A | 8/1996 | Imran |
| 5,562,100 | A | 10/1996 | Kittrell et al. |

(56) References Cited

U.S. PATENT DOCUMENTS

| | | | |
|---|---|---|---|
| 5,571,088 A * | 11/1996 | Lennox | A61B 8/12 604/96.01 |
| 5,571,122 A | 11/1996 | Kelly et al. | |
| 5,571,151 A | 11/1996 | Gregory | |
| 5,573,531 A | 11/1996 | Gregory et al. | |
| 5,573,533 A | 11/1996 | Strul | |
| 5,584,831 A | 12/1996 | McKay | |
| 5,584,872 A | 12/1996 | Lafontaine et al. | |
| 5,588,962 A | 12/1996 | Nicholas et al. | |
| 5,599,346 A | 2/1997 | Edwards et al. | |
| 5,601,526 A | 2/1997 | Chapelon et al. | |
| 5,609,606 A | 3/1997 | O'Boyle et al. | |
| 5,613,979 A | 3/1997 | Trotta et al. | |
| 5,626,576 A | 5/1997 | Janssen | |
| 5,630,837 A | 5/1997 | Crowley | |
| 5,637,090 A | 6/1997 | McGee et al. | |
| 5,643,255 A | 7/1997 | Organ | |
| 5,643,297 A | 7/1997 | Nordgren et al. | |
| 5,647,847 A | 7/1997 | Lafontaine et al. | |
| 5,649,923 A | 7/1997 | Gregory et al. | |
| 5,651,780 A | 7/1997 | Jackson et al. | |
| 5,653,684 A | 8/1997 | Laptewicz et al. | |
| 5,662,671 A | 9/1997 | Barbut et al. | |
| 5,665,062 A | 9/1997 | Houser | |
| 5,665,098 A | 9/1997 | Kelly et al. | |
| 5,666,964 A | 9/1997 | Meilus | |
| 5,667,490 A | 9/1997 | Keith et al. | |
| 5,672,174 A | 9/1997 | Gough et al. | |
| 5,676,693 A | 10/1997 | Lafontaine | |
| 5,678,296 A | 10/1997 | Fleischhacker et al. | |
| 5,681,282 A | 10/1997 | Eggers et al. | |
| RE35,656 E | 11/1997 | Feinberg | |
| 5,687,737 A | 11/1997 | Branham et al. | |
| 5,688,266 A | 11/1997 | Edwards et al. | |
| 5,693,015 A | 12/1997 | Walker et al. | |
| 5,693,029 A | 12/1997 | Leonhardt et al. | |
| 5,693,043 A | 12/1997 | Kittrell et al. | |
| 5,693,082 A | 12/1997 | Warner et al. | |
| 5,695,504 A | 12/1997 | Gifford et al. | |
| 5,697,369 A | 12/1997 | Long, Jr. et al. | |
| 5,697,909 A | 12/1997 | Eggers et al. | |
| 5,702,386 A | 12/1997 | Stern et al. | |
| 5,702,433 A | 12/1997 | Taylor et al. | |
| 5,706,809 A | 1/1998 | Littmann et al. | |
| 5,713,942 A | 2/1998 | Stern et al. | |
| 5,715,819 A | 2/1998 | Svenson et al. | |
| 5,735,846 A | 4/1998 | Panescu et al. | |
| 5,741,214 A | 4/1998 | Ouchi et al. | |
| 5,741,248 A | 4/1998 | Stern et al. | |
| 5,741,249 A | 4/1998 | Moss et al. | |
| 5,743,903 A | 4/1998 | Stern et al. | |
| 5,748,347 A | 5/1998 | Erickson | |
| 5,749,914 A | 5/1998 | Janssen | |
| 5,755,682 A | 5/1998 | Knudson et al. | |
| 5,755,715 A | 5/1998 | Stern et al. | |
| 5,755,753 A | 5/1998 | Knowlton et al. | |
| 5,769,847 A | 6/1998 | Panescu et al. | |
| 5,769,880 A | 6/1998 | Truckai et al. | |
| 5,775,338 A | 7/1998 | Hastings | |
| 5,776,174 A | 7/1998 | Van Tassel | |
| 5,779,698 A | 7/1998 | Clayman et al. | |
| 5,782,760 A | 7/1998 | Schaer | |
| 5,785,702 A | 7/1998 | Murphy et al. | |
| 5,797,849 A | 8/1998 | Vesely et al. | |
| 5,797,903 A | 8/1998 | Swanson et al. | |
| 5,800,484 A | 9/1998 | Gough et al. | |
| 5,800,494 A | 9/1998 | Campbell et al. | |
| 5,807,306 A | 9/1998 | Shapland et al. | |
| 5,810,802 A | 9/1998 | Panescu et al. | |
| 5,810,803 A | 9/1998 | Moss et al. | |
| 5,810,810 A | 9/1998 | Tay et al. | |
| 5,817,092 A | 10/1998 | Behl | |
| 5,817,113 A | 10/1998 | Gifford et al. | |
| 5,817,144 A | 10/1998 | Gregory et al. | |
| 5,823,956 A | 10/1998 | Roth et al. | |
| 5,827,203 A | 10/1998 | Nita et al. | |
| 5,827,268 A | 10/1998 | Laufer | |
| 5,829,447 A | 11/1998 | Stevens et al. | |
| 5,830,213 A | 11/1998 | Panescu et al. | |
| 5,830,222 A | 11/1998 | Makower | |
| 5,832,228 A | 11/1998 | Holden et al. | |
| 5,833,593 A | 11/1998 | Liprie | |
| 5,836,874 A | 11/1998 | Swanson et al. | |
| 5,840,076 A | 11/1998 | Swanson et al. | |
| 5,843,016 A | 12/1998 | Lugnani et al. | |
| 5,846,238 A | 12/1998 | Jackson et al. | |
| 5,846,239 A | 12/1998 | Swanson et al. | |
| 5,846,245 A | 12/1998 | McCarthy et al. | |
| 5,848,969 A | 12/1998 | Panescu et al. | |
| 5,853,411 A | 12/1998 | Whayne et al. | |
| 5,855,614 A | 1/1999 | Stevens et al. | |
| 5,860,974 A | 1/1999 | Abele | |
| 5,865,801 A | 2/1999 | Houser | |
| 5,868,735 A | 2/1999 | Lafontaine et al. | |
| 5,868,736 A | 2/1999 | Swanson et al. | |
| 5,871,483 A | 2/1999 | Jackson et al. | |
| 5,871,524 A | 2/1999 | Knowlton et al. | |
| 5,875,782 A | 3/1999 | Ferrari et al. | |
| 5,876,369 A | 3/1999 | Houser | |
| 5,876,374 A | 3/1999 | Alba et al. | |
| 5,876,397 A | 3/1999 | Edelman et al. | |
| 5,879,348 A | 3/1999 | Owens et al. | |
| 5,891,114 A | 4/1999 | Chien et al. | |
| 5,891,135 A | 4/1999 | Jackson et al. | |
| 5,891,136 A | 4/1999 | McGee et al. | |
| 5,891,138 A | 4/1999 | Tu et al. | |
| 5,895,378 A | 4/1999 | Nita | |
| 5,897,552 A | 4/1999 | Edwards et al. | |
| 5,902,328 A | 5/1999 | Lafontaine et al. | |
| 5,904,651 A | 5/1999 | Swanson et al. | |
| 5,904,667 A | 5/1999 | Falwell et al. | |
| 5,904,697 A | 5/1999 | Gifford et al. | |
| 5,904,709 A | 5/1999 | Arndt et al. | |
| 5,906,614 A | 5/1999 | Stern et al. | |
| 5,906,623 A | 5/1999 | Peterson | |
| 5,906,636 A | 5/1999 | Casscells et al. | |
| 5,916,192 A | 6/1999 | Nita et al. | |
| 5,916,227 A | 6/1999 | Keith et al. | |
| 5,916,239 A | 6/1999 | Geddes et al. | |
| 5,919,219 A | 7/1999 | Knowlton et al. | |
| 5,924,424 A | 7/1999 | Stevens et al. | |
| 5,925,038 A | 7/1999 | Panescu et al. | |
| 5,934,284 A | 8/1999 | Plaia et al. | |
| 5,935,063 A | 8/1999 | Nguyen | |
| 5,938,670 A | 8/1999 | Keith et al. | |
| 5,947,977 A | 9/1999 | Slepian et al. | |
| 5,948,011 A | 9/1999 | Knowlton et al. | |
| 5,951,494 A | 9/1999 | Wang et al. | |
| 5,951,539 A | 9/1999 | Nita et al. | |
| 5,954,717 A | 9/1999 | Behl et al. | |
| 5,957,882 A | 9/1999 | Nita et al. | |
| 5,957,941 A | 9/1999 | Ream et al. | |
| 5,957,969 A | 9/1999 | Warner et al. | |
| 5,961,513 A | 10/1999 | Swanson et al. | |
| 5,964,757 A | 10/1999 | Ponzi et al. | |
| 5,967,976 A | 10/1999 | Larsen et al. | |
| 5,967,978 A | 10/1999 | Littmann et al. | |
| 5,967,984 A | 10/1999 | Chu et al. | |
| 5,971,975 A | 10/1999 | Mills et al. | |
| 5,972,026 A | 10/1999 | Laufer et al. | |
| 5,980,563 A | 11/1999 | Tu et al. | |
| 5,989,208 A | 11/1999 | Nita et al. | |
| 5,989,284 A | 11/1999 | Laufer | |
| 5,993,462 A | 11/1999 | Pomeranz et al. | |
| 5,997,497 A | 12/1999 | Nita et al. | |
| 5,999,678 A | 12/1999 | Murphy et al. | |
| 6,004,269 A | 12/1999 | Crowley et al. | |
| 6,004,316 A | 12/1999 | Laufer et al. | |
| 6,007,514 A | 12/1999 | Nita | |
| 6,010,522 A | 1/2000 | Barbut et al. | |
| 6,013,033 A | 1/2000 | Berger et al. | |
| 6,014,590 A | 1/2000 | Whayne et al. | |
| 6,022,309 A | 2/2000 | Celliers et al. | |
| 6,024,740 A | 2/2000 | Lesh | |

(56) References Cited

U.S. PATENT DOCUMENTS

| | | | |
|---|---|---|---|
| 6,030,611 A | 2/2000 | Gorecki et al. |
| 6,032,675 A | 3/2000 | Rubinsky et al. |
| 6,033,397 A | 3/2000 | Laufer et al. |
| 6,033,398 A | 3/2000 | Farley et al. |
| 6,036,687 A | 3/2000 | Laufer et al. |
| 6,036,689 A | 3/2000 | Tu et al. |
| 6,041,260 A | 3/2000 | Stern et al. |
| 6,050,994 A | 4/2000 | Sherman et al. |
| 6,056,744 A | 5/2000 | Edwards |
| 6,056,746 A | 5/2000 | Goble et al. |
| 6,063,085 A | 5/2000 | Tay et al. |
| 6,066,096 A | 5/2000 | Smith et al. |
| 6,066,139 A | 5/2000 | Ryan et al. |
| 6,068,638 A | 5/2000 | Makower |
| 6,068,653 A | 5/2000 | Lafontaine |
| 6,071,277 A | 6/2000 | Farley et al. |
| 6,071,278 A | 6/2000 | Panescu et al. |
| 6,078,839 A | 6/2000 | Carson |
| 6,079,414 A | 6/2000 | Roth |
| 6,080,171 A | 6/2000 | Keith et al. |
| 6,081,749 A | 6/2000 | Ingle et al. |
| 6,086,581 A | 7/2000 | Reynolds et al. |
| 6,091,995 A | 7/2000 | Ingle et al. |
| 6,093,166 A | 7/2000 | Knudson et al. |
| 6,096,021 A | 8/2000 | Helm et al. |
| 6,099,526 A | 8/2000 | Whayne et al. |
| 6,102,908 A | 8/2000 | Tu et al. |
| 6,106,477 A | 8/2000 | Miesel et al. |
| 6,110,187 A | 8/2000 | Donlon et al. |
| 6,110,192 A | 8/2000 | Ravenscroft et al. |
| 6,114,311 A | 9/2000 | Parmacek et al. |
| 6,117,101 A | 9/2000 | Diederich et al. |
| 6,117,128 A | 9/2000 | Gregory |
| 6,120,476 A | 9/2000 | Fung et al. |
| 6,120,516 A | 9/2000 | Selmon et al. |
| 6,121,775 A | 9/2000 | Pearlman |
| 6,123,679 A | 9/2000 | Lafaut et al. |
| 6,123,682 A | 9/2000 | Knudson et al. |
| 6,123,702 A | 9/2000 | Swanson et al. |
| 6,123,703 A | 9/2000 | Tu et al. |
| 6,123,718 A | 9/2000 | Tu et al. |
| 6,129,725 A | 10/2000 | Tu et al. |
| 6,135,997 A | 10/2000 | Laufer et al. |
| 6,142,991 A | 11/2000 | Schatzberger et al. |
| 6,142,993 A | 11/2000 | Whayne et al. |
| 6,149,647 A | 11/2000 | Tu et al. |
| 6,152,899 A | 11/2000 | Farley et al. |
| 6,152,912 A | 11/2000 | Jansen et al. |
| 6,156,046 A | 12/2000 | Passafaro et al. |
| 6,158,250 A | 12/2000 | Tibbals et al. |
| 6,159,187 A | 12/2000 | Park et al. |
| 6,159,225 A | 12/2000 | Makower |
| 6,161,048 A | 12/2000 | Sluijter et al. |
| 6,162,184 A | 12/2000 | Swanson et al. |
| 6,165,163 A | 12/2000 | Chien et al. |
| 6,165,172 A | 12/2000 | Farley et al. |
| 6,165,187 A | 12/2000 | Reger et al. |
| 6,168,594 B1 | 1/2001 | Lafontaine et al. |
| 6,171,321 B1 | 1/2001 | Gifford, III et al. |
| 6,179,832 B1 | 1/2001 | Jones et al. |
| 6,179,835 B1 | 1/2001 | Panescu et al. |
| 6,179,859 B1 | 1/2001 | Bates et al. |
| 6,183,468 B1 | 2/2001 | Swanson et al. |
| 6,183,486 B1 | 2/2001 | Snow et al. |
| 6,190,379 B1 | 2/2001 | Heuser et al. |
| 6,191,862 B1 | 2/2001 | Swanson et al. |
| 6,197,021 B1 | 3/2001 | Panescu et al. |
| 6,200,266 B1 | 3/2001 | Shokrollahi et al. |
| 6,203,537 B1 | 3/2001 | Adrian |
| 6,203,561 B1 | 3/2001 | Ramee et al. |
| 6,210,406 B1 | 4/2001 | Webster |
| 6,211,247 B1 | 4/2001 | Goodman |
| 6,217,576 B1 | 4/2001 | Tu et al. |
| 6,219,577 B1 | 4/2001 | Brown, III et al. |
| 6,228,076 B1 | 5/2001 | Winston et al. |
| 6,228,109 B1 | 5/2001 | Tu et al. |
| 6,231,516 B1 | 5/2001 | Keilman et al. |
| 6,231,587 B1 | 5/2001 | Makower |
| 6,235,044 B1 | 5/2001 | Root et al. |
| 6,236,883 B1 | 5/2001 | Ciaccio et al. |
| 6,237,605 B1 | 5/2001 | Vaska et al. |
| 6,238,389 B1 | 5/2001 | Paddock et al. |
| 6,238,392 B1 * | 5/2001 | Long ............... A61B 18/1485 604/101.05 |
| 6,241,666 B1 | 6/2001 | Pomeranz et al. |
| 6,241,753 B1 | 6/2001 | Knowlton |
| 6,245,020 B1 | 6/2001 | Moore et al. |
| 6,245,045 B1 | 6/2001 | Stratienko |
| 6,248,126 B1 | 6/2001 | Lesser et al. |
| 6,251,128 B1 | 6/2001 | Knopp et al. |
| 6,258,087 B1 | 7/2001 | Edwards et al. |
| 6,273,886 B1 | 8/2001 | Edwards et al. |
| 6,280,466 B1 | 8/2001 | Kugler et al. |
| 6,283,935 B1 | 9/2001 | Laufer et al. |
| 6,283,959 B1 | 9/2001 | Lalonde et al. |
| 6,284,743 B1 | 9/2001 | Parmacek et al. |
| 6,287,323 B1 | 9/2001 | Hammerslag |
| 6,290,696 B1 | 9/2001 | Lafontaine |
| 6,292,695 B1 | 9/2001 | Webster, Jr. et al. |
| 6,293,942 B1 | 9/2001 | Goble et al. |
| 6,293,943 B1 | 9/2001 | Panescu et al. |
| 6,296,619 B1 | 10/2001 | Brisken et al. |
| 6,298,256 B1 | 10/2001 | Meyer |
| 6,299,379 B1 | 10/2001 | Lewis |
| 6,299,623 B1 | 10/2001 | Wulfman |
| 6,309,379 B1 | 10/2001 | Willard et al. |
| 6,309,399 B1 | 10/2001 | Barbut et al. |
| 6,311,090 B1 | 10/2001 | Knowlton |
| 6,317,615 B1 | 11/2001 | KenKnight et al. |
| 6,319,242 B1 | 11/2001 | Patterson et al. |
| 6,319,251 B1 | 11/2001 | Tu et al. |
| 6,322,559 B1 | 11/2001 | Daulton et al. |
| 6,325,797 B1 | 12/2001 | Stewart et al. |
| 6,325,799 B1 | 12/2001 | Goble |
| 6,328,699 B1 | 12/2001 | Eigler et al. |
| 6,346,074 B1 | 2/2002 | Roth |
| 6,346,104 B2 | 2/2002 | Daly et al. |
| 6,350,248 B1 | 2/2002 | Knudson et al. |
| 6,350,276 B1 | 2/2002 | Knowlton |
| 6,353,751 B1 | 3/2002 | Swanson et al. |
| 6,355,029 B1 | 3/2002 | Joye et al. |
| 6,357,447 B1 | 3/2002 | Swanson et al. |
| 6,361,519 B1 | 3/2002 | Knudson et al. |
| 6,364,840 B1 | 4/2002 | Crowley |
| 6,371,965 B2 | 4/2002 | Gifford, III et al. |
| 6,375,668 B1 * | 4/2002 | Gifford ............ A61B 17/12022 606/200 |
| 6,377,854 B1 | 4/2002 | Knowlton |
| 6,377,855 B1 | 4/2002 | Knowlton |
| 6,379,352 B1 | 4/2002 | Reynolds et al. |
| 6,379,373 B1 | 4/2002 | Sawhney et al. |
| 6,381,497 B1 | 4/2002 | Knowlton |
| 6,381,498 B1 | 4/2002 | Knowlton |
| 6,383,151 B1 | 5/2002 | Diederich et al. |
| 6,387,105 B1 | 5/2002 | Gifford, III et al. |
| 6,387,380 B1 | 5/2002 | Knowlton |
| 6,389,311 B1 | 5/2002 | Whayne et al. |
| 6,389,314 B2 | 5/2002 | Feiring |
| 6,391,024 B1 | 5/2002 | Sun et al. |
| 6,394,096 B1 | 5/2002 | Constantz |
| 6,394,956 B1 | 5/2002 | Chandrasekaran et al. |
| 6,398,780 B1 | 6/2002 | Farley et al. |
| 6,398,782 B1 | 6/2002 | Pecor et al. |
| 6,398,792 B1 | 6/2002 | O'Connor |
| 6,401,720 B1 | 6/2002 | Stevens et al. |
| 6,402,719 B1 | 6/2002 | Ponzi et al. |
| 6,405,090 B1 | 6/2002 | Knowlton |
| 6,409,723 B1 | 6/2002 | Edwards |
| 6,413,255 B1 | 7/2002 | Stern |
| 6,421,559 B1 | 7/2002 | Pearlman |
| 6,423,057 B1 | 7/2002 | He et al. |
| 6,425,867 B1 | 7/2002 | Vaezy et al. |
| 6,425,912 B1 | 7/2002 | Knowlton |
| 6,427,118 B1 | 7/2002 | Suzuki |

(56) References Cited

U.S. PATENT DOCUMENTS

| | | |
|---|---|---|
| 6,428,534 B1 | 8/2002 | Joye et al. |
| 6,428,536 B2 | 8/2002 | Panescu et al. |
| 6,430,446 B1 | 8/2002 | Knowlton |
| 6,432,102 B2 | 8/2002 | Joye et al. |
| 6,436,056 B1 | 8/2002 | Wang et al. |
| 6,438,424 B1 | 8/2002 | Knowlton |
| 6,440,125 B1 | 8/2002 | Rentrop |
| 6,442,413 B1 | 8/2002 | Silver |
| 6,443,965 B1 | 9/2002 | Gifford, III et al. |
| 6,445,939 B1 | 9/2002 | Swanson et al. |
| 6,447,505 B2 | 9/2002 | McGovern et al. |
| 6,447,509 B1 | 9/2002 | Bonnet et al. |
| 6,451,034 B1 | 9/2002 | Gifford, III et al. |
| 6,451,044 B1 | 9/2002 | Naghavi et al. |
| 6,453,202 B1 | 9/2002 | Knowlton |
| 6,454,737 B1 | 9/2002 | Nita et al. |
| 6,454,757 B1 | 9/2002 | Nita et al. |
| 6,454,775 B1 | 9/2002 | Demarais et al. |
| 6,458,098 B1 | 10/2002 | Kanesaka |
| 6,461,378 B1 | 10/2002 | Knowlton |
| 6,468,276 B1 | 10/2002 | McKay |
| 6,468,297 B1 | 10/2002 | Williams et al. |
| 6,470,216 B1 | 10/2002 | Knowlton |
| 6,470,219 B1 | 10/2002 | Edwards et al. |
| 6,471,696 B1 | 10/2002 | Berube et al. |
| 6,475,213 B1 | 11/2002 | Whayne et al. |
| 6,475,215 B1 | 11/2002 | Tanrisever |
| 6,475,238 B1 | 11/2002 | Fedida et al. |
| 6,477,426 B1 | 11/2002 | Fenn et al. |
| 6,480,745 B2 | 11/2002 | Nelson et al. |
| 6,481,704 B1 | 11/2002 | Koster et al. |
| 6,482,202 B1 | 11/2002 | Goble et al. |
| 6,484,052 B1 | 11/2002 | Visuri et al. |
| 6,485,489 B2 | 11/2002 | Teirstein et al. |
| 6,488,679 B1 | 12/2002 | Swanson et al. |
| 6,489,307 B1 | 12/2002 | Phillips et al. |
| 6,491,705 B2 | 12/2002 | Gifford, III et al. |
| 6,494,891 B1 | 12/2002 | Cornish et al. |
| 6,497,711 B1 | 12/2002 | Plaia et al. |
| 6,500,172 B1 | 12/2002 | Panescu et al. |
| 6,500,174 B1 | 12/2002 | Maguire et al. |
| 6,508,765 B2 | 1/2003 | Suorsa et al. |
| 6,508,804 B2 | 1/2003 | Sarge et al. |
| 6,508,815 B1 | 1/2003 | Strul et al. |
| 6,511,478 B1 | 1/2003 | Burnside et al. |
| 6,511,496 B1 | 1/2003 | Huter et al. |
| 6,511,500 B1 | 1/2003 | Rahme |
| 6,514,236 B1 | 2/2003 | Stratienko |
| 6,514,245 B1 | 2/2003 | Williams et al. |
| 6,514,248 B1 | 2/2003 | Eggers et al. |
| 6,517,534 B1 | 2/2003 | McGovern et al. |
| 6,517,572 B2 | 2/2003 | Kugler et al. |
| 6,522,913 B2 | 2/2003 | Swanson et al. |
| 6,522,926 B1 | 2/2003 | Kieval et al. |
| 6,524,299 B1 | 2/2003 | Tran et al. |
| 6,527,765 B2 | 3/2003 | Kelman et al. |
| 6,527,769 B2 | 3/2003 | Langberg et al. |
| 6,540,761 B2 | 4/2003 | Houser |
| 6,542,781 B1 | 4/2003 | Koblish et al. |
| 6,544,780 B1 | 4/2003 | Wang |
| 6,546,272 B1 | 4/2003 | MacKinnon et al. |
| 6,547,788 B1 | 4/2003 | Maguire et al. |
| 6,549,800 B1 | 4/2003 | Atalar et al. |
| 6,552,796 B2 | 4/2003 | Magnin et al. |
| 6,554,780 B1 | 4/2003 | Sampson et al. |
| 6,558,381 B2 | 5/2003 | Ingle et al. |
| 6,558,382 B2 | 5/2003 | Jahns et al. |
| 6,564,096 B2 | 5/2003 | Mest |
| 6,565,582 B2 | 5/2003 | Gifford, III et al. |
| 6,569,109 B2 | 5/2003 | Sakurai et al. |
| 6,569,177 B1 | 5/2003 | Dillard et al. |
| 6,570,659 B2 | 5/2003 | Schmitt |
| 6,572,551 B1 | 6/2003 | Smith et al. |
| 6,572,612 B2 | 6/2003 | Stewart et al. |
| 6,577,902 B1 | 6/2003 | Laufer et al. |
| 6,579,308 B1 | 6/2003 | Jansen et al. |
| 6,579,311 B1 | 6/2003 | Makower |
| 6,582,423 B1 | 6/2003 | Thapliyal et al. |
| 6,589,238 B2 | 7/2003 | Edwards et al. |
| 6,592,526 B1 | 7/2003 | Lenker |
| 6,592,567 B1 | 7/2003 | Levin et al. |
| 6,595,959 B1 | 7/2003 | Stratienko |
| 6,600,956 B2 | 7/2003 | Maschino et al. |
| 6,602,242 B1 | 8/2003 | Fung |
| 6,602,246 B1 | 8/2003 | Joye et al. |
| 6,605,056 B2 | 8/2003 | Eidenschink et al. |
| 6,605,084 B2 | 8/2003 | Acker et al. |
| 6,623,452 B2 | 9/2003 | Chien et al. |
| 6,623,453 B1 | 9/2003 | Guibert et al. |
| 6,632,193 B1 | 10/2003 | Davison et al. |
| 6,632,196 B1 | 10/2003 | Houser |
| 6,645,223 B2 | 11/2003 | Boyle et al. |
| 6,648,854 B1 | 11/2003 | Patterson et al. |
| 6,648,878 B2 | 11/2003 | Lafontaine |
| 6,648,879 B2 | 11/2003 | Joye et al. |
| 6,651,672 B2 | 11/2003 | Roth |
| 6,652,513 B2 | 11/2003 | Panescu et al. |
| 6,652,515 B1 | 11/2003 | Maguire et al. |
| 6,656,136 B1 | 12/2003 | Weng et al. |
| 6,658,279 B2 | 12/2003 | Swanson et al. |
| 6,659,981 B2 | 12/2003 | Stewart et al. |
| 6,666,858 B2 | 12/2003 | Lafontaine |
| 6,666,863 B2 | 12/2003 | Wentzel et al. |
| 6,669,655 B1 | 12/2003 | Acker et al. |
| 6,669,692 B1 | 12/2003 | Nelson et al. |
| 6,673,040 B1 | 1/2004 | Samson et al. |
| 6,673,064 B1 | 1/2004 | Rentrop |
| 6,673,066 B2 | 1/2004 | Werneth |
| 6,673,090 B2 | 1/2004 | Root et al. |
| 6,673,101 B1 | 1/2004 | Fitzgerald et al. |
| 6,673,290 B1 | 1/2004 | Whayne et al. |
| 6,676,678 B2 | 1/2004 | Gifford, III et al. |
| 6,679,268 B2 | 1/2004 | Stevens et al. |
| 6,681,773 B2 | 1/2004 | Murphy et al. |
| 6,682,541 B1 | 1/2004 | Gifford, III et al. |
| 6,684,098 B2 | 1/2004 | Oshio et al. |
| 6,685,732 B2 | 2/2004 | Kramer |
| 6,685,733 B1 | 2/2004 | Dae et al. |
| 6,689,086 B1 | 2/2004 | Nita et al. |
| 6,689,148 B2 | 2/2004 | Sawhney et al. |
| 6,690,181 B1 | 2/2004 | Dowdeswell et al. |
| 6,692,490 B1 | 2/2004 | Edwards |
| 6,695,830 B2 | 2/2004 | Vigil et al. |
| 6,695,857 B2 | 2/2004 | Gifford, III et al. |
| 6,699,241 B2 | 3/2004 | Rappaport et al. |
| 6,699,257 B2 | 3/2004 | Gifford, III et al. |
| 6,702,748 B1 | 3/2004 | Nita et al. |
| 6,702,811 B2 | 3/2004 | Stewart et al. |
| 6,706,010 B1 | 3/2004 | Miki et al. |
| 6,706,011 B1 | 3/2004 | Murphy-Chutorian et al. |
| 6,706,037 B2 | 3/2004 | Zvuloni et al. |
| 6,709,431 B2 | 3/2004 | Lafontaine |
| 6,711,429 B1 | 3/2004 | Gilboa et al. |
| 6,712,815 B2 | 3/2004 | Sampson et al. |
| 6,714,822 B2 | 3/2004 | King et al. |
| 6,716,184 B2 | 4/2004 | Vaezy et al. |
| 6,720,350 B2 | 4/2004 | Kunz et al. |
| 6,723,043 B2 | 4/2004 | Kleeman et al. |
| 6,723,064 B2 | 4/2004 | Babaev |
| 6,736,811 B2 | 5/2004 | Panescu et al. |
| 6,743,184 B2 | 6/2004 | Sampson et al. |
| 6,746,401 B2 | 6/2004 | Panescu |
| 6,746,464 B1 | 6/2004 | Makower |
| 6,746,474 B2 | 6/2004 | Saadat |
| 6,748,953 B2 | 6/2004 | Sherry et al. |
| 6,749,607 B2 | 6/2004 | Edwards et al. |
| 6,752,805 B2 | 6/2004 | Maguire et al. |
| 6,760,616 B2 | 7/2004 | Hoey et al. |
| 6,763,261 B2 | 7/2004 | Casscells, III et al. |
| 6,764,501 B2 | 7/2004 | Ganz |
| 6,769,433 B2 | 8/2004 | Zikorus et al. |
| 6,770,070 B1 | 8/2004 | Balbierz |
| 6,771,996 B2 | 8/2004 | Bowe et al. |
| 6,773,433 B2 | 8/2004 | Stewart et al. |

(56) References Cited

U.S. PATENT DOCUMENTS

| | | |
|---|---|---|
| 6,786,900 B2 | 9/2004 | Joye et al. |
| 6,786,901 B2 | 9/2004 | Joye et al. |
| 6,786,904 B2 | 9/2004 | Döscher et al. |
| 6,788,977 B2 | 9/2004 | Fenn et al. |
| 6,790,206 B2 | 9/2004 | Panescu |
| 6,790,222 B2 | 9/2004 | Kugler et al. |
| 6,796,981 B2 | 9/2004 | Wham et al. |
| 6,797,933 B1 | 9/2004 | Mendis et al. |
| 6,797,960 B1 | 9/2004 | Spartiotis et al. |
| 6,800,075 B2 | 10/2004 | Mische et al. |
| 6,802,857 B1 | 10/2004 | Walsh et al. |
| 6,807,444 B2 | 10/2004 | Tu et al. |
| 6,811,550 B2 | 11/2004 | Holland et al. |
| 6,813,520 B2 | 11/2004 | Truckai et al. |
| 6,814,730 B2 | 11/2004 | Li |
| 6,814,733 B2 | 11/2004 | Schwartz et al. |
| 6,823,205 B1 | 11/2004 | Jara |
| 6,824,516 B2 | 11/2004 | Batten et al. |
| 6,827,726 B2 | 12/2004 | Parodi |
| 6,827,926 B2 | 12/2004 | Robinson et al. |
| 6,829,497 B2 | 12/2004 | Mogul |
| 6,830,568 B1 | 12/2004 | Kesten et al. |
| 6,837,886 B2 | 1/2005 | Collins et al. |
| 6,837,888 B2 | 1/2005 | Ciarrocca et al. |
| 6,845,267 B2 | 1/2005 | Harrison |
| 6,847,848 B2 | 1/2005 | Sterzer |
| 6,849,073 B2 | 2/2005 | Hoey et al. |
| 6,849,075 B2 | 2/2005 | Bertolero et al. |
| 6,853,425 B2 | 2/2005 | Kim et al. |
| 6,855,123 B2 | 2/2005 | Nita |
| 6,855,143 B2 | 2/2005 | Davison |
| 6,869,431 B2 | 3/2005 | Maguire et al. |
| 6,872,183 B2 | 3/2005 | Sampson et al. |
| 6,884,260 B2 | 4/2005 | Kugler et al. |
| 6,889,694 B2 | 5/2005 | Hooven |
| 6,893,436 B2 | 5/2005 | Woodard et al. |
| 6,895,077 B2 | 5/2005 | Karellas et al. |
| 6,895,265 B2 | 5/2005 | Silver |
| 6,898,454 B2 | 5/2005 | Atalar et al. |
| 6,899,711 B2 | 5/2005 | Stewart et al. |
| 6,899,718 B2 | 5/2005 | Gifford, III et al. |
| 6,905,494 B2 | 6/2005 | Yon et al. |
| 6,908,462 B2 | 6/2005 | Joye et al. |
| 6,909,009 B2 | 6/2005 | Koridze |
| 6,911,026 B1 | 6/2005 | Hall et al. |
| 6,915,806 B2 | 7/2005 | Pacek et al. |
| 6,923,805 B1 | 8/2005 | LaFontaine et al. |
| 6,923,808 B2 | 8/2005 | Taimisto |
| 6,926,246 B2 | 8/2005 | Ginggen |
| 6,926,713 B2 | 8/2005 | Rioux et al. |
| 6,926,716 B2 | 8/2005 | Baker et al. |
| 6,929,009 B2 | 8/2005 | Makower et al. |
| 6,929,632 B2 | 8/2005 | Nita et al. |
| 6,929,639 B2 | 8/2005 | Lafontaine |
| 6,932,776 B2 | 8/2005 | Carr |
| 6,936,047 B2 | 8/2005 | Nasab et al. |
| 6,942,620 B2 | 9/2005 | Nita et al. |
| 6,942,657 B2 | 9/2005 | Sinofsky et al. |
| 6,942,677 B2 | 9/2005 | Nita et al. |
| 6,942,692 B2 | 9/2005 | Landau et al. |
| 6,949,097 B2 | 9/2005 | Stewart et al. |
| 6,949,121 B1 | 9/2005 | Laguna |
| 6,952,615 B2 | 10/2005 | Satake |
| 6,953,425 B2 | 10/2005 | Brister |
| 6,955,174 B2 | 10/2005 | Joye et al. |
| 6,955,175 B2 | 10/2005 | Stevens et al. |
| 6,959,711 B2 | 11/2005 | Murphy et al. |
| 6,960,207 B2 | 11/2005 | Vanney et al. |
| 6,962,584 B1 | 11/2005 | Stone et al. |
| 6,964,660 B2 | 11/2005 | Maguire et al. |
| 6,966,908 B2 | 11/2005 | Maguire et al. |
| 6,972,015 B2 | 12/2005 | Joye et al. |
| 6,972,024 B1 | 12/2005 | Kilpatrick et al. |
| 6,974,456 B2 | 12/2005 | Edwards et al. |
| 6,978,174 B2 | 12/2005 | Gelfand et al. |
| 6,979,329 B2 | 12/2005 | Burnside et al. |
| 6,979,420 B2 | 12/2005 | Weber |
| 6,984,238 B2 | 1/2006 | Gifford, III et al. |
| 6,985,774 B2 | 1/2006 | Kieval et al. |
| 6,986,739 B2 | 1/2006 | Warren et al. |
| 6,989,009 B2 | 1/2006 | Lafontaine |
| 6,989,010 B2 | 1/2006 | Francischelli et al. |
| 6,991,617 B2 | 1/2006 | Hektner et al. |
| 7,001,378 B2 | 2/2006 | Yon et al. |
| 7,006,858 B2 | 2/2006 | Silver et al. |
| 7,022,105 B1 | 4/2006 | Edwards |
| 7,022,120 B2 | 4/2006 | Lafontaine |
| 7,025,767 B2 | 4/2006 | Schaefer et al. |
| 7,033,322 B2 | 4/2006 | Silver |
| 7,033,372 B1 | 4/2006 | Cahalan |
| 7,041,098 B2 | 5/2006 | Farley et al. |
| 7,050,848 B2 | 5/2006 | Hoey et al. |
| 7,063,670 B2 | 6/2006 | Sampson et al. |
| 7,063,679 B2 | 6/2006 | Maguire et al. |
| 7,063,719 B2 | 6/2006 | Jansen et al. |
| 7,066,895 B2 | 6/2006 | Podany |
| 7,066,900 B2 | 6/2006 | Botto et al. |
| 7,066,904 B2 | 6/2006 | Rosenthal et al. |
| 7,072,720 B2 | 7/2006 | Puskas |
| 7,074,217 B2 | 7/2006 | Strul et al. |
| 7,081,112 B2 | 7/2006 | Joye et al. |
| 7,081,114 B2 | 7/2006 | Rashidi |
| 7,083,614 B2 | 8/2006 | Fjield et al. |
| 7,084,276 B2 | 8/2006 | Vu et al. |
| 7,087,026 B2 | 8/2006 | Callister et al. |
| 7,087,051 B2 | 8/2006 | Bourne et al. |
| 7,087,052 B2 | 8/2006 | Sampson et al. |
| 7,087,053 B2 | 8/2006 | Vanney |
| 7,089,065 B2 | 8/2006 | Westlund et al. |
| 7,097,641 B1 | 8/2006 | Arless et al. |
| 7,100,614 B2 | 9/2006 | Stevens et al. |
| 7,101,368 B2 | 9/2006 | Lafontaine |
| 7,104,983 B2 | 9/2006 | Grasso, III et al. |
| 7,104,987 B2 | 9/2006 | Biggs et al. |
| 7,108,715 B2 | 9/2006 | Lawrence-Brown et al. |
| 7,112,196 B2 | 9/2006 | Brosch et al. |
| 7,112,198 B2 | 9/2006 | Satake |
| 7,112,211 B2 | 9/2006 | Gifford, III et al. |
| 7,122,019 B1 | 10/2006 | Kesten et al. |
| 7,122,033 B2 | 10/2006 | Wood |
| 7,134,438 B2 | 11/2006 | Makower et al. |
| 7,137,963 B2 | 11/2006 | Nita et al. |
| 7,137,980 B2 | 11/2006 | Buysse et al. |
| 7,153,315 B2 | 12/2006 | Miller |
| 7,155,271 B2 | 12/2006 | Halperin et al. |
| 7,157,491 B2 | 1/2007 | Mewshaw et al. |
| 7,157,492 B2 | 1/2007 | Mewshaw et al. |
| 7,158,832 B2 | 1/2007 | Kieval et al. |
| 7,160,296 B2 | 1/2007 | Pearson et al. |
| 7,162,303 B2 | 1/2007 | Levin et al. |
| 7,165,551 B2 | 1/2007 | Edwards et al. |
| 7,169,144 B2 | 1/2007 | Hoey et al. |
| 7,172,589 B2 | 2/2007 | Lafontaine |
| 7,172,610 B2 | 2/2007 | Heitzmann et al. |
| 7,181,261 B2 | 2/2007 | Silver et al. |
| 7,184,811 B2 | 2/2007 | Phan et al. |
| 7,184,827 B1 | 2/2007 | Edwards |
| 7,189,227 B2 | 3/2007 | Lafontaine |
| 7,192,427 B2 | 3/2007 | Chapelon et al. |
| 7,192,586 B2 | 3/2007 | Bander |
| 7,197,354 B2 | 3/2007 | Sobe |
| 7,198,632 B2 | 4/2007 | Lim et al. |
| 7,200,445 B1 | 4/2007 | Dalbec et al. |
| 7,201,749 B2 | 4/2007 | Govari et al. |
| 7,203,537 B2 | 4/2007 | Mower |
| 7,214,234 B2 | 5/2007 | Rapacki et al. |
| 7,220,233 B2 | 5/2007 | Nita et al. |
| 7,220,239 B2 | 5/2007 | Wilson et al. |
| 7,220,257 B1 | 5/2007 | Lafontaine |
| 7,220,270 B2 | 5/2007 | Sawhney et al. |
| 7,232,458 B2 | 6/2007 | Saadat |
| 7,232,459 B2 | 6/2007 | Greenberg et al. |
| 7,238,184 B2 | 7/2007 | Megerman et al. |
| 7,241,273 B2 | 7/2007 | Maguire et al. |

(56) References Cited

U.S. PATENT DOCUMENTS

| | | |
|---|---|---|
| 7,241,736 B2 | 7/2007 | Hunter et al. |
| 7,247,141 B2 | 7/2007 | Makin et al. |
| 7,250,041 B2 | 7/2007 | Chiu et al. |
| 7,250,440 B2 | 7/2007 | Mewshaw et al. |
| 7,252,664 B2 | 8/2007 | Nasab et al. |
| 7,252,679 B2 | 8/2007 | Fischell et al. |
| 7,264,619 B2 | 9/2007 | Venturelli |
| 7,279,600 B2 | 10/2007 | Mewshaw et al. |
| 7,280,863 B2 | 10/2007 | Shachar |
| 7,282,213 B2 | 10/2007 | Schroeder et al. |
| 7,285,119 B2 | 10/2007 | Stewart et al. |
| 7,285,120 B2 | 10/2007 | Im et al. |
| 7,288,089 B2 | 10/2007 | Yon et al. |
| 7,288,096 B2 | 10/2007 | Chin |
| 7,291,146 B2 | 11/2007 | Steinke et al. |
| 7,293,562 B2 | 11/2007 | Malecki et al. |
| 7,294,125 B2 | 11/2007 | Phalen et al. |
| 7,294,126 B2 | 11/2007 | Sampson et al. |
| 7,294,127 B2 | 11/2007 | Leung et al. |
| 7,297,131 B2 | 11/2007 | Nita |
| 7,297,475 B2 | 11/2007 | Koiwai et al. |
| 7,300,433 B2 | 11/2007 | Lane et al. |
| 7,301,108 B2 | 11/2007 | Egitto et al. |
| 7,310,150 B2 | 12/2007 | Guillermo et al. |
| 7,313,430 B2 | 12/2007 | Urquhart et al. |
| 7,314,480 B2 | 1/2008 | Eidenschink et al. |
| 7,314,483 B2 | 1/2008 | Landau et al. |
| 7,317,077 B2 | 1/2008 | Averback et al. |
| 7,323,006 B2 | 1/2008 | Andreas et al. |
| 7,326,206 B2 | 2/2008 | Paul et al. |
| 7,326,226 B2 | 2/2008 | Root et al. |
| 7,326,235 B2 | 2/2008 | Edwards |
| 7,326,237 B2 | 2/2008 | DePalma et al. |
| 7,329,236 B2 | 2/2008 | Kesten et al. |
| 7,335,180 B2 | 2/2008 | Nita et al. |
| 7,335,192 B2 | 2/2008 | Keren et al. |
| 7,338,467 B2 | 3/2008 | Lutter |
| 7,341,570 B2 | 3/2008 | Keren et al. |
| 7,343,195 B2 | 3/2008 | Strommer et al. |
| 7,347,857 B2 | 3/2008 | Anderson et al. |
| 7,348,003 B2 | 3/2008 | Salcedo et al. |
| 7,352,593 B2 | 4/2008 | Zeng et al. |
| 7,354,927 B2 | 4/2008 | Vu |
| 7,359,732 B2 | 4/2008 | Kim et al. |
| 7,361,341 B2 | 4/2008 | Salcedo et al. |
| 7,364,566 B2 | 4/2008 | Elkins et al. |
| 7,367,970 B2 | 5/2008 | Govari et al. |
| 7,367,975 B2 | 5/2008 | Malecki et al. |
| 7,371,231 B2 | 5/2008 | Rioux et al. |
| 7,387,126 B2 | 6/2008 | Cox et al. |
| 7,393,338 B2 | 7/2008 | Nita |
| 7,396,355 B2 | 7/2008 | Goldman et al. |
| 7,402,151 B2 | 7/2008 | Rosenman et al. |
| 7,402,312 B2 | 7/2008 | Rosen et al. |
| 7,404,824 B1 | 7/2008 | Webler et al. |
| 7,406,970 B2 | 8/2008 | Zikorus et al. |
| 7,407,502 B2 | 8/2008 | Strul et al. |
| 7,407,506 B2 | 8/2008 | Makower |
| 7,407,671 B2 | 8/2008 | McBride et al. |
| 7,408,021 B2 | 8/2008 | Averback et al. |
| 7,410,486 B2 | 8/2008 | Fuimaono et al. |
| 7,413,556 B2 | 8/2008 | Zhang et al. |
| 7,425,212 B1 | 9/2008 | Danek et al. |
| 7,426,409 B2 | 9/2008 | Casscells, III et al. |
| 7,435,248 B2 | 10/2008 | Taimisto et al. |
| 7,447,453 B2 | 11/2008 | Kim et al. |
| 7,449,018 B2 | 11/2008 | Kramer |
| 7,452,538 B2 | 11/2008 | Ni et al. |
| 7,473,890 B2 | 1/2009 | Grier et al. |
| 7,476,384 B2 | 1/2009 | Ni et al. |
| 7,479,157 B2 | 1/2009 | Weber et al. |
| 7,481,803 B2 | 1/2009 | Kesten et al. |
| 7,485,104 B2 | 2/2009 | Kieval |
| 7,486,805 B2 | 2/2009 | Krattiger |
| 7,487,780 B2 | 2/2009 | Hooven |
| 7,493,154 B2 | 2/2009 | Bonner et al. |
| 7,494,485 B2 | 2/2009 | Beck et al. |
| 7,494,486 B2 | 2/2009 | Mische et al. |
| 7,494,488 B2 | 2/2009 | Weber |
| 7,494,661 B2 | 2/2009 | Sanders |
| 7,495,439 B2 | 2/2009 | Wiggins |
| 7,497,858 B2 | 3/2009 | Chapelon et al. |
| 7,499,745 B2 | 3/2009 | Littrup et al. |
| 7,500,985 B2 | 3/2009 | Saadat |
| 7,505,812 B1 | 3/2009 | Eggers et al. |
| 7,505,816 B2 | 3/2009 | Schmeling et al. |
| 7,507,233 B2 | 3/2009 | Littrup et al. |
| 7,507,235 B2 | 3/2009 | Keogh et al. |
| 7,511,494 B2 | 3/2009 | Wedeen |
| 7,512,445 B2 | 3/2009 | Truckai et al. |
| 7,527,643 B2 | 5/2009 | Case et al. |
| 7,529,589 B2 | 5/2009 | Williams et al. |
| 7,540,852 B2 | 6/2009 | Nita et al. |
| 7,540,870 B2 | 6/2009 | Babaev |
| RE40,863 E | 7/2009 | Tay et al. |
| 7,556,624 B2 | 7/2009 | Laufer et al. |
| 7,558,625 B2 | 7/2009 | Levin et al. |
| 7,563,247 B2 | 7/2009 | Maguire et al. |
| 7,566,319 B2 | 7/2009 | McAuley et al. |
| 7,569,052 B2 | 8/2009 | Phan et al. |
| 7,582,111 B2 | 9/2009 | Krolik et al. |
| 7,584,004 B2 | 9/2009 | Caparso et al. |
| 7,585,835 B2 | 9/2009 | Hill et al. |
| 7,591,996 B2 | 9/2009 | Hwang et al. |
| 7,597,704 B2 | 10/2009 | Frazier et al. |
| 7,598,228 B2 | 10/2009 | Hattori et al. |
| 7,599,730 B2 | 10/2009 | Hunter et al. |
| 7,603,166 B2 | 10/2009 | Casscells, III et al. |
| 7,604,608 B2 | 10/2009 | Nita et al. |
| 7,604,633 B2 | 10/2009 | Truckai et al. |
| 7,615,015 B2 | 11/2009 | Coleman |
| 7,615,072 B2 | 11/2009 | Rust et al. |
| 7,617,005 B2 | 11/2009 | Demarais et al. |
| 7,620,451 B2 | 11/2009 | Demarais et al. |
| 7,621,902 B2 | 11/2009 | Nita et al. |
| 7,621,929 B2 | 11/2009 | Nita et al. |
| 7,626,015 B2 | 12/2009 | Feinstein et al. |
| 7,626,235 B2 | 12/2009 | Kinoshita |
| 7,632,268 B2 | 12/2009 | Edwards et al. |
| 7,632,845 B2 | 12/2009 | Vu et al. |
| 7,635,383 B2 | 12/2009 | Gumm |
| 7,640,046 B2 | 12/2009 | Pastore et al. |
| 7,641,633 B2 | 1/2010 | Laufer et al. |
| 7,641,679 B2 | 1/2010 | Joye et al. |
| 7,646,544 B2 | 1/2010 | Batchko et al. |
| 7,647,115 B2 | 1/2010 | Levin et al. |
| 7,653,438 B2 | 1/2010 | Deem et al. |
| 7,655,006 B2 | 2/2010 | Sauvageau et al. |
| 7,662,114 B2 | 2/2010 | Seip et al. |
| 7,664,548 B2 | 2/2010 | Amurthur et al. |
| 7,670,279 B2 | 3/2010 | Gertner |
| 7,670,335 B2 | 3/2010 | Keidar |
| 7,671,084 B2 | 3/2010 | Mewshaw et al. |
| 7,678,104 B2 | 3/2010 | Keidar |
| 7,678,106 B2 | 3/2010 | Lee |
| 7,678,108 B2 | 3/2010 | Chrisitian et al. |
| 7,686,841 B2 | 3/2010 | Eidenschink et al. |
| 7,691,080 B2 | 4/2010 | Seward et al. |
| 7,699,809 B2 | 4/2010 | Urmey |
| 7,706,882 B2 | 4/2010 | Francischelli et al. |
| 7,715,912 B2 | 5/2010 | Rezai et al. |
| 7,717,853 B2 | 5/2010 | Nita |
| 7,717,909 B2 | 5/2010 | Strul et al. |
| 7,717,948 B2 | 5/2010 | Demarais et al. |
| 7,722,539 B2 | 5/2010 | Carter et al. |
| 7,725,157 B2 | 5/2010 | Dumoulin et al. |
| 7,727,178 B2 | 6/2010 | Wilson et al. |
| 7,736,317 B2 | 6/2010 | Stephens et al. |
| 7,736,360 B2 | 6/2010 | Mody et al. |
| 7,736,362 B2 | 6/2010 | Eberl et al. |
| 7,738,952 B2 | 6/2010 | Yun et al. |
| 7,740,629 B2 | 6/2010 | Anderson et al. |
| 7,741,299 B2 | 6/2010 | Feinstein et al. |
| 7,742,795 B2 | 6/2010 | Stone et al. |

(56) References Cited

U.S. PATENT DOCUMENTS

| | | |
|---|---|---|
| 7,744,594 B2 | 6/2010 | Yamazaki et al. |
| 7,753,907 B2 | 7/2010 | DiMatteo et al. |
| 7,756,583 B2 | 7/2010 | Demarais et al. |
| 7,758,510 B2 | 7/2010 | Nita et al. |
| 7,758,520 B2 | 7/2010 | Griffin et al. |
| 7,759,315 B2 | 7/2010 | Cuzzocrea et al. |
| 7,766,833 B2 | 8/2010 | Lee et al. |
| 7,766,878 B2 | 8/2010 | Tremaglio, Jr. et al. |
| 7,766,892 B2 | 8/2010 | Keren et al. |
| 7,767,844 B2 | 8/2010 | Lee et al. |
| 7,769,427 B2 | 8/2010 | Shachar |
| 7,771,372 B2 | 8/2010 | Wilson |
| 7,771,421 B2 | 8/2010 | Stewart et al. |
| 7,776,967 B2 | 8/2010 | Perry et al. |
| 7,777,486 B2 | 8/2010 | Hargreaves et al. |
| 7,780,660 B2 | 8/2010 | Bourne et al. |
| 7,789,876 B2 | 9/2010 | Zikorus et al. |
| 7,792,568 B2 | 9/2010 | Zhong et al. |
| 7,799,021 B2 | 9/2010 | Leung et al. |
| 7,803,168 B2 | 9/2010 | Gifford et al. |
| 7,806,871 B2 | 10/2010 | Li et al. |
| 7,811,265 B2 | 10/2010 | Hering et al. |
| 7,811,281 B1 | 10/2010 | Rentrop |
| 7,811,313 B2 | 10/2010 | Mon et al. |
| 7,816,511 B2 | 10/2010 | Kawashima et al. |
| 7,818,053 B2 | 10/2010 | Kassab |
| 7,819,866 B2 | 10/2010 | Bednarek |
| 7,822,460 B2 | 10/2010 | Halperin et al. |
| 7,828,837 B2 | 11/2010 | Khoury |
| 7,832,407 B2 | 11/2010 | Gertner |
| 7,833,220 B2 | 11/2010 | Mon et al. |
| 7,837,676 B2 | 11/2010 | Sinelnikov et al. |
| 7,837,720 B2 | 11/2010 | Mon |
| 7,841,978 B2 | 11/2010 | Gertner |
| 7,846,157 B2 | 12/2010 | Kozel |
| 7,846,160 B2 | 12/2010 | Payne et al. |
| 7,846,172 B2 | 12/2010 | Makower |
| 7,849,860 B2 | 12/2010 | Makower et al. |
| 7,850,685 B2 | 12/2010 | Kunis et al. |
| 7,853,333 B2 | 12/2010 | Demarais |
| 7,854,734 B2 | 12/2010 | Biggs et al. |
| 7,857,756 B2 | 12/2010 | Warren et al. |
| 7,862,565 B2 | 1/2011 | Eder et al. |
| 7,863,897 B2 | 1/2011 | Slocum, Jr. et al. |
| 7,869,854 B2 | 1/2011 | Shachar et al. |
| 7,873,417 B2 | 1/2011 | Demarais et al. |
| 7,887,538 B2 | 2/2011 | Bleich et al. |
| 7,894,905 B2 | 2/2011 | Pless et al. |
| 7,896,873 B2 | 3/2011 | Hiller et al. |
| 7,901,400 B2 | 3/2011 | Wham et al. |
| 7,901,402 B2 | 3/2011 | Jones et al. |
| 7,901,420 B2 | 3/2011 | Dunn |
| 7,905,862 B2 | 3/2011 | Sampson |
| 7,918,850 B2 | 4/2011 | Govari et al. |
| 7,927,370 B2 | 4/2011 | Webler et al. |
| 7,937,143 B2 | 5/2011 | Demarais et al. |
| 7,938,830 B2 | 5/2011 | Saadat et al. |
| 7,942,874 B2 | 5/2011 | Eder et al. |
| 7,942,928 B2 | 5/2011 | Webler et al. |
| 7,946,976 B2 | 5/2011 | Gertner |
| 7,950,397 B2 | 5/2011 | Thapliyal et al. |
| 7,955,293 B2 | 6/2011 | Nita et al. |
| 7,956,613 B2 | 6/2011 | Wald |
| 7,959,627 B2 | 6/2011 | Utley et al. |
| 7,962,854 B2 | 6/2011 | Vance et al. |
| 7,967,782 B2 | 6/2011 | Laufer et al. |
| 7,967,808 B2 | 6/2011 | Fitzgerald et al. |
| 7,972,327 B2 | 7/2011 | Eberl et al. |
| 7,972,330 B2 | 7/2011 | Alejandro et al. |
| 7,983,751 B2 | 7/2011 | Zdeblick et al. |
| 8,001,976 B2 | 8/2011 | Gertner |
| 8,007,440 B2 | 8/2011 | Magnin et al. |
| 8,012,147 B2 | 9/2011 | Lafontaine |
| 8,019,435 B2 | 9/2011 | Hastings et al. |
| 8,021,362 B2 | 9/2011 | Deem et al. |
| 8,021,413 B2 | 9/2011 | Dierking et al. |
| 8,025,661 B2 | 9/2011 | Arnold et al. |
| 8,027,718 B2 | 9/2011 | Spinner et al. |
| 8,031,927 B2 | 10/2011 | Karl et al. |
| 8,033,284 B2 | 10/2011 | Porter et al. |
| 8,043,673 B2 | 10/2011 | Lee et al. |
| 8,048,144 B2 | 11/2011 | Thistle et al. |
| 8,052,636 B2 | 11/2011 | Moll et al. |
| 8,052,700 B2 | 11/2011 | Dunn |
| 8,062,289 B2 | 11/2011 | Babaev |
| 8,075,580 B2 | 12/2011 | Makower |
| 8,080,006 B2 | 12/2011 | Lafontaine et al. |
| 8,088,127 B2 | 1/2012 | Mayse et al. |
| 8,116,883 B2 | 2/2012 | Williams et al. |
| 8,119,183 B2 | 2/2012 | O'Donoghue et al. |
| 8,120,518 B2 | 2/2012 | Jang et al. |
| 8,123,741 B2 | 2/2012 | Marrouche et al. |
| 8,128,617 B2 | 3/2012 | Bencini et al. |
| 8,131,371 B2 | 3/2012 | Demarals et al. |
| 8,131,372 B2 | 3/2012 | Levin et al. |
| 8,131,382 B2 | 3/2012 | Asada |
| 8,137,274 B2 | 3/2012 | Weng et al. |
| 8,140,170 B2 | 3/2012 | Rezai et al. |
| 8,143,316 B2 | 3/2012 | Ueno |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,152,830 B2 | 4/2012 | Gumm |
| 8,162,933 B2 | 4/2012 | Francischelli et al. |
| 8,168,275 B2 | 5/2012 | Lee et al. |
| 8,175,711 B2 | 5/2012 | Demarais et al. |
| 8,187,261 B2 | 5/2012 | Watson |
| 8,190,238 B2 | 5/2012 | Moll et al. |
| 8,192,053 B2 | 6/2012 | Owen et al. |
| 8,198,611 B2 | 6/2012 | LaFontaine et al. |
| 8,214,056 B2 | 7/2012 | Hoffer et al. |
| 8,221,407 B2 | 7/2012 | Phan et al. |
| 8,226,637 B2 | 7/2012 | Satake |
| 8,231,617 B2 | 7/2012 | Satake |
| 8,241,217 B2 | 8/2012 | Chiang et al. |
| 8,257,724 B2 | 9/2012 | Cromack et al. |
| 8,257,725 B2 | 9/2012 | Cromack et al. |
| 8,260,397 B2 | 9/2012 | Ruff et al. |
| 8,263,104 B2 | 9/2012 | Ho et al. |
| 8,273,023 B2 | 9/2012 | Razavi |
| 8,277,379 B2 | 10/2012 | Lau et al. |
| 8,287,524 B2 | 10/2012 | Siegel |
| 8,287,532 B2 | 10/2012 | Carroll et al. |
| 8,292,881 B2 | 10/2012 | Brannan et al. |
| 8,293,703 B2 | 10/2012 | Averback et al. |
| 8,295,902 B2 | 10/2012 | Salahieh et al. |
| 8,295,912 B2 | 10/2012 | Gertner |
| 8,308,722 B2 | 11/2012 | Ormsby et al. |
| 8,317,776 B2 | 11/2012 | Ferren et al. |
| 8,317,810 B2 | 11/2012 | Stangenes et al. |
| 8,329,179 B2 | 12/2012 | Ni et al. |
| 8,336,705 B2 | 12/2012 | Okahisa |
| 8,343,031 B2 | 1/2013 | Gertner |
| 8,343,145 B2 | 1/2013 | Brannan |
| 8,347,891 B2 | 1/2013 | Demarais et al. |
| 8,353,945 B2 | 1/2013 | Andreas et al. |
| 8,364,237 B2 | 1/2013 | Stone et al. |
| 8,366,615 B2 | 2/2013 | Razavi |
| 8,382,697 B2 | 2/2013 | Brenneman et al. |
| 8,388,680 B2 | 3/2013 | Starksen et al. |
| 8,396,548 B2 | 3/2013 | Perry et al. |
| 8,398,629 B2 | 3/2013 | Thistle |
| 8,401,667 B2 | 3/2013 | Gustus et al. |
| 8,403,881 B2 | 3/2013 | Ferren et al. |
| 8,406,877 B2 | 3/2013 | Smith et al. |
| 8,409,172 B2 | 4/2013 | Moll et al. |
| 8,409,193 B2 | 4/2013 | Young et al. |
| 8,409,195 B2 | 4/2013 | Young |
| 8,418,362 B2 | 4/2013 | Zerfas et al. |
| 8,452,988 B2 | 5/2013 | Wang |
| 8,454,594 B2 | 6/2013 | Demarais et al. |
| 8,460,358 B2 | 6/2013 | Andreas et al. |

(56) References Cited

U.S. PATENT DOCUMENTS

| | | |
|---|---|---|
| 8,465,452 B2 | 6/2013 | Kassab |
| 8,469,919 B2 | 6/2013 | Ingle et al. |
| 8,473,067 B2 | 6/2013 | Hastings et al. |
| 8,480,663 B2 | 7/2013 | Ingle et al. |
| 8,485,992 B2 | 7/2013 | Griffin et al. |
| 8,486,060 B2 | 7/2013 | Kotmel et al. |
| 8,486,063 B2 | 7/2013 | Werneth et al. |
| 8,488,591 B2 | 7/2013 | Miali et al. |
| 2001/0007070 A1 | 7/2001 | Stewart et al. |
| 2001/0039419 A1 | 11/2001 | Francischelli et al. |
| 2002/0022864 A1 | 2/2002 | Mahvi et al. |
| 2002/0042639 A1 | 4/2002 | Murphy-Chutorian et al. |
| 2002/0045811 A1 | 4/2002 | Kittrell et al. |
| 2002/0045890 A1 | 4/2002 | Celliers et al. |
| 2002/0062146 A1 | 5/2002 | Makower et al. |
| 2002/0065542 A1 | 5/2002 | Lax et al. |
| 2002/0087151 A1 | 7/2002 | Mody et al. |
| 2002/0095197 A1 | 7/2002 | Lardo et al. |
| 2002/0107536 A1 | 8/2002 | Hussein |
| 2002/0147480 A1 | 10/2002 | Mamayek |
| 2002/0169444 A1 | 11/2002 | Mest et al. |
| 2002/0198520 A1 | 12/2002 | Coen et al. |
| 2003/0050635 A1 | 3/2003 | Truckai et al. |
| 2003/0065317 A1 | 4/2003 | Rudie et al. |
| 2003/0092995 A1 | 5/2003 | Thompson |
| 2003/0139689 A1 | 7/2003 | Shturman et al. |
| 2003/0195501 A1 | 10/2003 | Sherman et al. |
| 2003/0199747 A1 | 10/2003 | Michlitsch et al. |
| 2003/0229340 A1 | 12/2003 | Sherry et al. |
| 2003/0233099 A1 | 12/2003 | Danaek et al. |
| 2004/0010118 A1 | 1/2004 | Zerhusen et al. |
| 2004/0019348 A1 | 1/2004 | Stevens et al. |
| 2004/0024371 A1 | 2/2004 | Plicchi et al. |
| 2004/0043030 A1 | 3/2004 | Griffiths et al. |
| 2004/0064090 A1 | 4/2004 | Keren et al. |
| 2004/0073206 A1 | 4/2004 | Foley et al. |
| 2004/0082859 A1* | 4/2004 | Schaer ............... A61B 8/4281 600/459 |
| 2004/0088002 A1 | 5/2004 | Boyle et al. |
| 2004/0093055 A1 | 5/2004 | Bartorelli et al. |
| 2004/0106871 A1 | 6/2004 | Hunyor et al. |
| 2004/0117032 A1 | 6/2004 | Roth |
| 2004/0147915 A1 | 7/2004 | Hasebe |
| 2004/0162555 A1 | 8/2004 | Farley et al. |
| 2004/0167506 A1 | 8/2004 | Chen |
| 2004/0186356 A1 | 9/2004 | O'Malley et al. |
| 2004/0187875 A1 | 9/2004 | He et al. |
| 2004/0193211 A1 | 9/2004 | Voegele et al. |
| 2004/0220556 A1 | 11/2004 | Cooper et al. |
| 2004/0243022 A1 | 12/2004 | Carney et al. |
| 2004/0253304 A1 | 12/2004 | Gross et al. |
| 2004/0267250 A1 | 12/2004 | Yon et al. |
| 2005/0010095 A1 | 1/2005 | Stewart et al. |
| 2005/0015125 A1 | 1/2005 | Mioduski et al. |
| 2005/0080374 A1 | 4/2005 | Esch et al. |
| 2005/0096647 A1 | 5/2005 | Steinke et al. |
| 2005/0129616 A1 | 6/2005 | Salcedo et al. |
| 2005/0137180 A1 | 6/2005 | Robinson et al. |
| 2005/0143817 A1 | 6/2005 | Hunter et al. |
| 2005/0148842 A1 | 7/2005 | Wang et al. |
| 2005/0149069 A1 | 7/2005 | Bertolero et al. |
| 2005/0149080 A1 | 7/2005 | Hunter et al. |
| 2005/0149158 A1 | 7/2005 | Hunter et al. |
| 2005/0149173 A1 | 7/2005 | Hunter et al. |
| 2005/0149175 A1 | 7/2005 | Hunter et al. |
| 2005/0154277 A1 | 7/2005 | Tang et al. |
| 2005/0154445 A1 | 7/2005 | Hunter et al. |
| 2005/0154453 A1 | 7/2005 | Hunter et al. |
| 2005/0154454 A1 | 7/2005 | Hunter et al. |
| 2005/0165389 A1 | 7/2005 | Swain et al. |
| 2005/0165391 A1 | 7/2005 | Maguire et al. |
| 2005/0165467 A1 | 7/2005 | Hunter et al. |
| 2005/0165488 A1 | 7/2005 | Hunter et al. |
| 2005/0175661 A1 | 8/2005 | Hunter et al. |
| 2005/0175662 A1 | 8/2005 | Hunter et al. |
| 2005/0175663 A1 | 8/2005 | Hunter et al. |
| 2005/0177103 A1 | 8/2005 | Hunter et al. |
| 2005/0177225 A1 | 8/2005 | Hunter et al. |
| 2005/0181004 A1 | 8/2005 | Hunter et al. |
| 2005/0181008 A1 | 8/2005 | Hunter et al. |
| 2005/0181011 A1 | 8/2005 | Hunter et al. |
| 2005/0181977 A1 | 8/2005 | Hunter et al. |
| 2005/0182479 A1 | 8/2005 | Bonsignore et al. |
| 2005/0183728 A1 | 8/2005 | Hunter et al. |
| 2005/0186242 A1 | 8/2005 | Hunter et al. |
| 2005/0186243 A1 | 8/2005 | Hunter et al. |
| 2005/0191331 A1 | 9/2005 | Hunter et al. |
| 2005/0203410 A1 | 9/2005 | Jenkins |
| 2005/0209587 A1 | 9/2005 | Joye et al. |
| 2005/0214205 A1 | 9/2005 | Salcedo et al. |
| 2005/0214207 A1 | 9/2005 | Salcedo et al. |
| 2005/0214208 A1 | 9/2005 | Salcedo et al. |
| 2005/0214209 A1 | 9/2005 | Salcedo et al. |
| 2005/0214210 A1 | 9/2005 | Salcedo et al. |
| 2005/0214268 A1 | 9/2005 | Cavanagh et al. |
| 2005/0228286 A1 | 10/2005 | Messerly et al. |
| 2005/0228415 A1 | 10/2005 | Gertner |
| 2005/0228460 A1 | 10/2005 | Levin et al. |
| 2005/0232921 A1 | 10/2005 | Rosen et al. |
| 2005/0234312 A1 | 10/2005 | Suzuki et al. |
| 2005/0245862 A1 | 11/2005 | Seward |
| 2005/0251116 A1 | 11/2005 | Steinke et al. |
| 2005/0252553 A1 | 11/2005 | Ginggen |
| 2005/0256398 A1 | 11/2005 | Hastings et al. |
| 2005/0267556 A1 | 12/2005 | Shuros et al. |
| 2005/0273149 A1 | 12/2005 | Tran et al. |
| 2006/0004323 A1 | 1/2006 | Chang et al. |
| 2006/0018949 A1 | 1/2006 | Ammon et al. |
| 2006/0024564 A1 | 2/2006 | Manclaw |
| 2006/0025765 A1 | 2/2006 | Landman et al. |
| 2006/0062786 A1 | 3/2006 | Salcedo et al. |
| 2006/0083194 A1 | 4/2006 | Dhrimaj et al. |
| 2006/0085054 A1 | 4/2006 | Zikorus et al. |
| 2006/0089637 A1 | 4/2006 | Werneth et al. |
| 2006/0089638 A1 | 4/2006 | Carmel et al. |
| 2006/0095096 A1 | 5/2006 | DeBenedictis et al. |
| 2006/0106375 A1 | 5/2006 | Werneth et al. |
| 2006/0142790 A1 | 6/2006 | Gertner |
| 2006/0142801 A1* | 6/2006 | Demarais ............... A61M 25/10 607/2 |
| 2006/0147492 A1 | 7/2006 | Hunter et al. |
| 2006/0167106 A1 | 7/2006 | Zhang et al. |
| 2006/0167498 A1 | 7/2006 | DiLorenzo |
| 2006/0171895 A1 | 8/2006 | Bucay-Couto |
| 2006/0182873 A1 | 8/2006 | Klisch et al. |
| 2006/0184221 A1 | 8/2006 | Stewart et al. |
| 2006/0195139 A1 | 8/2006 | Gertner |
| 2006/0206150 A1 | 9/2006 | Demarais et al. |
| 2006/0224153 A1 | 10/2006 | Fischell et al. |
| 2006/0239921 A1 | 10/2006 | Mangat et al. |
| 2006/0240070 A1 | 10/2006 | Cromack et al. |
| 2006/0247266 A1 | 11/2006 | Yamada et al. |
| 2006/0247760 A1 | 11/2006 | Ganesan et al. |
| 2006/0263393 A1 | 11/2006 | Demopulos et al. |
| 2006/0269555 A1 | 11/2006 | Salcedo et al. |
| 2006/0271111 A1 | 11/2006 | Demarais et al. |
| 2006/0287644 A1 | 12/2006 | Inganas et al. |
| 2007/0016184 A1 | 1/2007 | Cropper et al. |
| 2007/0016274 A1 | 1/2007 | Boveja et al. |
| 2007/0027390 A1 | 2/2007 | Maschke et al. |
| 2007/0043077 A1 | 2/2007 | Mewshaw et al. |
| 2007/0043409 A1 | 2/2007 | Brian et al. |
| 2007/0049924 A1 | 3/2007 | Rahn |
| 2007/0066972 A1 | 3/2007 | Ormsby et al. |
| 2007/0067883 A1 | 3/2007 | Sretavan |
| 2007/0073151 A1 | 3/2007 | Lee |
| 2007/0083192 A1* | 4/2007 | Welch ............... A61B 18/1492 606/41 |
| 2007/0093710 A1 | 4/2007 | Maschke |
| 2007/0100405 A1 | 5/2007 | Thompson et al. |
| 2007/0106247 A1 | 5/2007 | Burnett et al. |
| 2007/0112327 A1 | 5/2007 | Yun et al. |
| 2007/0118107 A1 | 5/2007 | Francischelli et al. |
| 2007/0129720 A1 | 6/2007 | Demarais et al. |

(56) References Cited

U.S. PATENT DOCUMENTS

| | | |
|---|---|---|
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0149963 A1* | 6/2007 | Matsukuma ............ A61B 18/04 606/28 |
| 2007/0162109 A1 | 7/2007 | Davila et al. |
| 2007/0173805 A1 | 7/2007 | Weinberg et al. |
| 2007/0179496 A1 | 8/2007 | Swoyer et al. |
| 2007/0203480 A1 | 8/2007 | Mody et al. |
| 2007/0207186 A1 | 9/2007 | Scanlon et al. |
| 2007/0208134 A1 | 9/2007 | Hunter et al. |
| 2007/0208210 A1 | 9/2007 | Gelfand et al. |
| 2007/0208256 A1 | 9/2007 | Marilla |
| 2007/0208301 A1 | 9/2007 | Evard et al. |
| 2007/0219576 A1 | 9/2007 | Cangialosi |
| 2007/0225781 A1 | 9/2007 | Saadat et al. |
| 2007/0233170 A1 | 10/2007 | Gertner |
| 2007/0239062 A1 | 10/2007 | Chopra et al. |
| 2007/0248639 A1 | 10/2007 | Demopulos et al. |
| 2007/0249703 A1 | 10/2007 | Mewshaw et al. |
| 2007/0254833 A1 | 11/2007 | Hunter et al. |
| 2007/0265687 A1 | 11/2007 | Deem et al. |
| 2007/0278103 A1 | 12/2007 | Hoerr et al. |
| 2007/0282302 A1 | 12/2007 | Wachsman et al. |
| 2007/0292411 A1 | 12/2007 | Salcedo et al. |
| 2007/0293782 A1 | 12/2007 | Marino |
| 2007/0299043 A1 | 12/2007 | Hunter et al. |
| 2008/0004673 A1 | 1/2008 | Rossing et al. |
| 2008/0009927 A1 | 1/2008 | Vilims |
| 2008/0015501 A1 | 1/2008 | Gertner |
| 2008/0021408 A1 | 1/2008 | Jacobsen et al. |
| 2008/0033049 A1 | 2/2008 | Mewshaw |
| 2008/0039746 A1 | 2/2008 | Hissong et al. |
| 2008/0039830 A1 | 2/2008 | Munger et al. |
| 2008/0051454 A1 | 2/2008 | Wang |
| 2008/0064957 A1 | 3/2008 | Spence |
| 2008/0071269 A1 | 3/2008 | Hilario et al. |
| 2008/0071306 A1 | 3/2008 | Gertner |
| 2008/0082109 A1 | 4/2008 | Moll et al. |
| 2008/0086072 A1 | 4/2008 | Bonutti et al. |
| 2008/0091193 A1 | 4/2008 | Kauphusman et al. |
| 2008/0097251 A1 | 4/2008 | Babaev |
| 2008/0097426 A1 | 4/2008 | Root et al. |
| 2008/0108867 A1 | 5/2008 | Zhou |
| 2008/0119879 A1 | 5/2008 | Brenneman et al. |
| 2008/0125772 A1 | 5/2008 | Stone et al. |
| 2008/0132450 A1 | 6/2008 | Lee et al. |
| 2008/0140002 A1 | 6/2008 | Ramzipoor et al. |
| 2008/0147002 A1 | 6/2008 | Gertner |
| 2008/0161662 A1 | 7/2008 | Golijanin et al. |
| 2008/0161717 A1 | 7/2008 | Gertner |
| 2008/0161801 A1 | 7/2008 | Steinke et al. |
| 2008/0171974 A1 | 7/2008 | Lafontaine et al. |
| 2008/0172035 A1 | 7/2008 | Starksen et al. |
| 2008/0172104 A1 | 7/2008 | Kieval et al. |
| 2008/0188912 A1 | 8/2008 | Stone et al. |
| 2008/0188913 A1 | 8/2008 | Stone et al. |
| 2008/0208162 A1 | 8/2008 | Joshi |
| 2008/0208169 A1 | 8/2008 | Boyle et al. |
| 2008/0213331 A1 | 9/2008 | Gelfand et al. |
| 2008/0215117 A1 | 9/2008 | Gross |
| 2008/0221448 A1 | 9/2008 | Khuri-Yakub et al. |
| 2008/0234790 A1 | 9/2008 | Bayer et al. |
| 2008/0243091 A1 | 10/2008 | Humphreys et al. |
| 2008/0245371 A1 | 10/2008 | Gruber |
| 2008/0249525 A1 | 10/2008 | Lee et al. |
| 2008/0249547 A1 | 10/2008 | Dunn |
| 2008/0255550 A1 | 10/2008 | Bell |
| 2008/0255642 A1 | 10/2008 | Zarins et al. |
| 2008/0262489 A1 | 10/2008 | Steinke |
| 2008/0275484 A1 | 11/2008 | Gertner |
| 2008/0281312 A1 | 11/2008 | Werneth et al. |
| 2008/0281347 A1 | 11/2008 | Gertner |
| 2008/0287918 A1 | 11/2008 | Rosenman et al. |
| 2008/0294037 A1 | 11/2008 | Richter |
| 2008/0300618 A1 | 12/2008 | Gertner |
| 2008/0312644 A1 | 12/2008 | Fourkas et al. |
| 2008/0312673 A1 | 12/2008 | Viswanathan et al. |
| 2008/0317818 A1 | 12/2008 | Griffith et al. |
| 2009/0018486 A1 | 1/2009 | Goren et al. |
| 2009/0018609 A1 | 1/2009 | DiLorenzo |
| 2009/0024194 A1 | 1/2009 | Arcot-Krishnamurthy et al. |
| 2009/0030312 A1 | 1/2009 | Hadjicostis |
| 2009/0036948 A1 | 2/2009 | Levin et al. |
| 2009/0043372 A1 | 2/2009 | Northrop et al. |
| 2009/0054082 A1 | 2/2009 | Kim et al. |
| 2009/0062873 A1 | 3/2009 | Wu et al. |
| 2009/0069671 A1 | 3/2009 | Anderson |
| 2009/0076409 A1 | 3/2009 | Wu et al. |
| 2009/0088735 A1 | 4/2009 | Abboud et al. |
| 2009/0105631 A1 | 4/2009 | Kieval |
| 2009/0112202 A1 | 4/2009 | Young |
| 2009/0118620 A1 | 5/2009 | Tgavalekos et al. |
| 2009/0118726 A1 | 5/2009 | Auth et al. |
| 2009/0125099 A1 | 5/2009 | Weber et al. |
| 2009/0131798 A1 | 5/2009 | Minar et al. |
| 2009/0143640 A1 | 6/2009 | Saadat et al. |
| 2009/0156988 A1 | 6/2009 | Ferren et al. |
| 2009/0157057 A1 | 6/2009 | Ferren et al. |
| 2009/0157161 A1 | 6/2009 | Desai et al. |
| 2009/0171333 A1 | 7/2009 | Hon |
| 2009/0192558 A1 | 7/2009 | Whitehurst et al. |
| 2009/0198223 A1 | 8/2009 | Thilwind et al. |
| 2009/0203962 A1 | 8/2009 | Miller et al. |
| 2009/0203993 A1 | 8/2009 | Mangat et al. |
| 2009/0204170 A1 | 8/2009 | Hastings et al. |
| 2009/0210953 A1 | 8/2009 | Moyer et al. |
| 2009/0216317 A1 | 8/2009 | Cromack et al. |
| 2009/0221955 A1 | 9/2009 | Babaev |
| 2009/0226429 A1 | 9/2009 | Salcedo et al. |
| 2009/0240249 A1 | 9/2009 | Chan et al. |
| 2009/0247933 A1 | 10/2009 | Maor et al. |
| 2009/0247966 A1 | 10/2009 | Gunn et al. |
| 2009/0248012 A1 | 10/2009 | Maor et al. |
| 2009/0253974 A1 | 10/2009 | Rahme |
| 2009/0264755 A1 | 10/2009 | Chen et al. |
| 2009/0270850 A1 | 10/2009 | Zhou et al. |
| 2009/0281533 A1 | 11/2009 | Ingle et al. |
| 2009/0287137 A1 | 11/2009 | Crowley |
| 2009/0318749 A1 | 12/2009 | Stolen et al. |
| 2010/0009267 A1 | 1/2010 | Chase et al. |
| 2010/0030061 A1 | 2/2010 | Canfield et al. |
| 2010/0048983 A1 | 2/2010 | Ball et al. |
| 2010/0049099 A1 | 2/2010 | Thapliyal et al. |
| 2010/0049186 A1 | 2/2010 | Ingle et al. |
| 2010/0049188 A1 | 2/2010 | Nelson et al. |
| 2010/0049191 A1 | 2/2010 | Habib et al. |
| 2010/0049283 A1 | 2/2010 | Johnson |
| 2010/0069837 A1 | 3/2010 | Rassat et al. |
| 2010/0076299 A1 | 3/2010 | Gustus et al. |
| 2010/0076425 A1 | 3/2010 | Carroux |
| 2010/0087782 A1 | 4/2010 | Ghaffari et al. |
| 2010/0106005 A1 | 4/2010 | Karczmar et al. |
| 2010/0114244 A1 | 5/2010 | Manda et al. |
| 2010/0130836 A1 | 5/2010 | Malchano et al. |
| 2010/0137860 A1 | 6/2010 | Demarais et al. |
| 2010/0137952 A1 | 6/2010 | Demarais et al. |
| 2010/0160903 A1 | 6/2010 | Krespi |
| 2010/0160906 A1 | 6/2010 | Jarrard |
| 2010/0168624 A1 | 7/2010 | Sliwa |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0191112 A1 | 7/2010 | Demarais et al. |
| 2010/0191232 A1 | 7/2010 | Boveda |
| 2010/0217162 A1 | 8/2010 | Hissong et al. |
| 2010/0222786 A1 | 9/2010 | Kassab |
| 2010/0222851 A1 | 9/2010 | Deem et al. |
| 2010/0222854 A1 | 9/2010 | Demarais et al. |
| 2010/0228122 A1 | 9/2010 | Keenan et al. |
| 2010/0249604 A1 | 9/2010 | Hastings et al. |
| 2010/0249773 A1 | 9/2010 | Clark et al. |
| 2010/0256616 A1 | 10/2010 | Katoh et al. |
| 2010/0268217 A1 | 10/2010 | Habib |

(56) References Cited

U.S. PATENT DOCUMENTS

| | | |
|---|---|---|
| 2010/0268307 A1 | 10/2010 | Demarais et al. |
| 2010/0284927 A1 | 11/2010 | Lu et al. |
| 2010/0286684 A1 | 11/2010 | Hata et al. |
| 2010/0298821 A1 | 11/2010 | Garbagnati |
| 2010/0305036 A1 | 12/2010 | Barnes et al. |
| 2010/0312141 A1 | 12/2010 | Keast et al. |
| 2010/0324472 A1 | 12/2010 | Wulfman |
| 2011/0009750 A1 | 1/2011 | Taylor et al. |
| 2011/0021976 A1 | 1/2011 | Li et al. |
| 2011/0034832 A1 | 2/2011 | Cioanta et al. |
| 2011/0040324 A1 | 2/2011 | McCarthy et al. |
| 2011/0044942 A1 | 2/2011 | Puri et al. |
| 2011/0060324 A1 | 3/2011 | Wu et al. |
| 2011/0071400 A1 | 3/2011 | Hastings et al. |
| 2011/0071401 A1 | 3/2011 | Hastings et al. |
| 2011/0077498 A1 | 3/2011 | McDaniel |
| 2011/0092781 A1 | 4/2011 | Gertner |
| 2011/0092880 A1 | 4/2011 | Gertner |
| 2011/0104061 A1 | 5/2011 | Seward |
| 2011/0112400 A1 | 5/2011 | Emery et al. |
| 2011/0118600 A1 | 5/2011 | Gertner |
| 2011/0118726 A1 | 5/2011 | De La Rama et al. |
| 2011/0130708 A1 | 6/2011 | Perry et al. |
| 2011/0137155 A1 | 6/2011 | Weber et al. |
| 2011/0144479 A1 | 6/2011 | Hastings et al. |
| 2011/0146673 A1 | 6/2011 | Keast et al. |
| 2011/0166499 A1 | 7/2011 | Demarais et al. |
| 2011/0178570 A1 | 7/2011 | Demarais |
| 2011/0200171 A1 | 8/2011 | Beetel et al. |
| 2011/0202098 A1 | 8/2011 | Demarais et al. |
| 2011/0207758 A1 | 8/2011 | Sobotka et al. |
| 2011/0208096 A1 | 8/2011 | Demarais et al. |
| 2011/0257523 A1 | 10/2011 | Hastings et al. |
| 2011/0257564 A1 | 10/2011 | Demarais et al. |
| 2011/0257622 A1 | 10/2011 | Salahieh et al. |
| 2011/0257641 A1 | 10/2011 | Hastings et al. |
| 2011/0257642 A1 | 10/2011 | Griggs, III |
| 2011/0263921 A1 | 10/2011 | Vrba et al. |
| 2011/0264011 A1 | 10/2011 | Wu et al. |
| 2011/0264075 A1 | 10/2011 | Leung et al. |
| 2011/0264086 A1 | 10/2011 | Ingle |
| 2011/0264116 A1 | 10/2011 | Kocur et al. |
| 2011/0270238 A1 | 11/2011 | Rizq et al. |
| 2011/0306851 A1 | 12/2011 | Wang |
| 2011/0319809 A1 | 12/2011 | Smith |
| 2012/0029496 A1 | 2/2012 | Smith |
| 2012/0029500 A1 | 2/2012 | Jenson |
| 2012/0029505 A1 | 2/2012 | Jenson |
| 2012/0029509 A1 | 2/2012 | Smith |
| 2012/0029510 A1 | 2/2012 | Haverkost |
| 2012/0029511 A1 | 2/2012 | Smith et al. |
| 2012/0029512 A1 | 2/2012 | Willard et al. |
| 2012/0029513 A1 | 2/2012 | Smith et al. |
| 2012/0059241 A1 | 3/2012 | Hastings et al. |
| 2012/0059286 A1 | 3/2012 | Hastings et al. |
| 2012/0065506 A1 | 3/2012 | Smith |
| 2012/0065554 A1 | 3/2012 | Pikus |
| 2012/0095461 A1 | 4/2012 | Herscher et al. |
| 2012/0101413 A1 | 4/2012 | Beetel et al. |
| 2012/0101490 A1 | 4/2012 | Smith |
| 2012/0101538 A1 | 4/2012 | Ballakur et al. |
| 2012/0109021 A1 | 5/2012 | Hastings et al. |
| 2012/0116382 A1 | 5/2012 | Ku et al. |
| 2012/0116383 A1 | 5/2012 | Mauch et al. |
| 2012/0116392 A1 | 5/2012 | Willard |
| 2012/0116438 A1 | 5/2012 | Salahieh et al. |
| 2012/0116486 A1 | 5/2012 | Naga et al. |
| 2012/0123243 A1 | 5/2012 | Hastings |
| 2012/0123258 A1 | 5/2012 | Willard |
| 2012/0123261 A1 | 5/2012 | Jenson et al. |
| 2012/0123303 A1 | 5/2012 | Sogard et al. |
| 2012/0123406 A1 | 5/2012 | Edmunds et al. |
| 2012/0130289 A1 | 5/2012 | Demarais et al. |
| 2012/0130345 A1 | 5/2012 | Levin et al. |
| 2012/0130359 A1 | 5/2012 | Turovskiy |
| 2012/0130360 A1 | 5/2012 | Buckley et al. |
| 2012/0130362 A1 | 5/2012 | Hastings et al. |
| 2012/0130368 A1 | 5/2012 | Jenson |
| 2012/0130458 A1 | 5/2012 | Ryba et al. |
| 2012/0136344 A1 | 5/2012 | Buckley et al. |
| 2012/0136349 A1 | 5/2012 | Hastings |
| 2012/0136350 A1 | 5/2012 | Goshgarian et al. |
| 2012/0136417 A1 | 5/2012 | Buckley et al. |
| 2012/0136418 A1 | 5/2012 | Buckley et al. |
| 2012/0143181 A1 | 6/2012 | Demarais et al. |
| 2012/0143293 A1 | 6/2012 | Mauch et al. |
| 2012/0143294 A1 | 6/2012 | Clark et al. |
| 2012/0150267 A1 | 6/2012 | Buckley et al. |
| 2012/0157986 A1 | 6/2012 | Stone et al. |
| 2012/0157987 A1 | 6/2012 | Steinke et al. |
| 2012/0157988 A1 | 6/2012 | Stone et al. |
| 2012/0157989 A1 | 6/2012 | Stone et al. |
| 2012/0157992 A1 | 6/2012 | Smith et al. |
| 2012/0157993 A1 | 6/2012 | Jenson et al. |
| 2012/0158101 A1 | 6/2012 | Stone et al. |
| 2012/0158104 A1 | 6/2012 | Huynh et al. |
| 2012/0172837 A1 | 7/2012 | Demarais et al. |
| 2012/0172870 A1 | 7/2012 | Jenson et al. |
| 2012/0184952 A1 | 7/2012 | Jenson et al. |
| 2012/0197198 A1 | 8/2012 | Demarais et al. |
| 2012/0197252 A1 | 8/2012 | Deem et al. |
| 2012/0232409 A1 | 9/2012 | Stahmann et al. |
| 2012/0265066 A1 | 10/2012 | Crow et al. |
| 2012/0265198 A1 | 10/2012 | Crow et al. |
| 2013/0012844 A1 | 1/2013 | Demarais et al. |
| 2013/0012866 A1 | 1/2013 | Deem et al. |
| 2013/0012867 A1 | 1/2013 | Demarais et al. |
| 2013/0013024 A1 | 1/2013 | Levin et al. |
| 2013/0023865 A1 | 1/2013 | Steinke et al. |
| 2013/0035681 A1 | 2/2013 | Subramanaim et al. |
| 2013/0066316 A1 | 3/2013 | Steinke et al. |
| 2013/0085489 A1 | 4/2013 | Fain et al. |
| 2013/0090563 A1 | 4/2013 | Weber |
| 2013/0090578 A1 | 4/2013 | Smith et al. |
| 2013/0090647 A1 | 4/2013 | Smith |
| 2013/0090649 A1 | 4/2013 | Smith et al. |
| 2013/0090650 A1 | 4/2013 | Jenson et al. |
| 2013/0090651 A1 | 4/2013 | Smith |
| 2013/0090652 A1 | 4/2013 | Jenson |
| 2013/0096550 A1 | 4/2013 | Hill |
| 2013/0096553 A1 | 4/2013 | Hill et al. |
| 2013/0096554 A1 | 4/2013 | Groff et al. |
| 2013/0096604 A1 | 4/2013 | Hanson et al. |
| 2013/0110106 A1 | 5/2013 | Richardson |
| 2013/0116687 A1 | 5/2013 | Willard |
| 2013/0165764 A1 | 6/2013 | Scheuermann et al. |
| 2013/0165844 A1 | 6/2013 | Shuros et al. |
| 2013/0165916 A1 | 6/2013 | Mathur et al. |
| 2013/0165917 A1 | 6/2013 | Mathur et al. |
| 2013/0165920 A1 | 6/2013 | Weber et al. |
| 2013/0165923 A1 | 6/2013 | Mathur et al. |
| 2013/0165924 A1 | 6/2013 | Mathur et al. |
| 2013/0165925 A1 | 6/2013 | Mathur et al. |
| 2013/0165926 A1 | 6/2013 | Mathur et al. |
| 2013/0165990 A1 | 6/2013 | Mathur et al. |
| 2013/0172815 A1 | 7/2013 | Perry et al. |
| 2013/0172872 A1 | 7/2013 | Subramaniam et al. |
| 2013/0172877 A1 | 7/2013 | Subramaniam et al. |
| 2013/0172878 A1 | 7/2013 | Smith |
| 2013/0172879 A1 | 7/2013 | Sutermeister |
| 2013/0172880 A1 | 7/2013 | Willard |
| 2013/0172881 A1 | 7/2013 | Hill et al. |
| 2014/0074083 A1 | 3/2014 | Horn et al. |

FOREIGN PATENT DOCUMENTS

| | | |
|---|---|---|
| EP | 1180004 A1 | 2/2002 |
| EP | 1335677 B1 | 8/2003 |
| EP | 1874211 A2 | 1/2008 |
| EP | 1906853 A2 | 4/2008 |
| EP | 1961394 A2 | 8/2008 |
| EP | 1620156 B1 | 7/2009 |
| EP | 2076193 A2 | 7/2009 |
| EP | 2091455 A2 | 8/2009 |

(56) References Cited

FOREIGN PATENT DOCUMENTS

| | | | |
|---|---|---|---|
| EP | 2197533 A1 | 6/2010 |
| EP | 2208506 A1 | 7/2010 |
| EP | 1579889 B1 | 8/2010 |
| EP | 2092957 B1 | 1/2011 |
| EP | 2349044 A1 | 8/2011 |
| EP | 2027882 B1 | 10/2011 |
| EP | 2378956 A2 | 10/2011 |
| EP | 2037840 B1 | 12/2011 |
| EP | 2204134 B1 | 4/2012 |
| EP | 2320821 B1 | 10/2012 |
| GB | 2456301 A | 7/2009 |
| WO | 9858588 A1 | 12/1998 |
| WO | 9900060 A1 | 1/1999 |
| WO | 9935986 | 7/1999 |
| WO | 0047118 A1 | 8/2000 |
| WO | 0066021 | 11/2000 |
| WO | 0195820 | 12/2001 |
| WO | 03026525 A1 | 4/2003 |
| WO | 2004100813 A2 | 11/2004 |
| WO | 2004110258 A2 | 12/2004 |
| WO | 2005041810 | 5/2005 |
| WO | 2006105121 A2 | 10/2006 |
| WO | 2008014465 A2 | 1/2008 |
| WO | 2009121017 A1 | 10/2009 |
| WO | 2010067360 A2 | 6/2010 |
| WO | 2010102310 A2 | 9/2010 |
| WO | 2010132703 | 11/2010 |
| WO | 2011005901 A2 | 1/2011 |
| WO | 2011053757 A1 | 5/2011 |
| WO | 2011053772 A1 | 5/2011 |
| WO | 2011091069 A1 | 7/2011 |
| WO | 2011130534 A2 | 10/2011 |
| WO | 2012019156 A1 | 2/2012 |
| WO | 2013049601 A2 | 4/2013 |

OTHER PUBLICATIONS

Van Den Berg, "Light echoes image the human body," OLE, Oct. 2001, p. 35-37.
"IntraLuminal: Products," IntraLuminal Therapeutics, Inc., 2003, p. 1-9.
"Laser Catheter to Aid Coronary Surgery," TechTalk: MIT, Jan. 9, 1991, p. 1-4.
"Optical Coherence Tomography: LightLab Imaging Starts US Cardiology Clinical Investigations," LightLab Imaging Technology, 2002.
"Optical Coherence Tomography: LightLab Sees Bright Prospects for Cardiac Application of OCT Technology," LightLab Imaging Technology, 2001, vol. 27, No. 35.
"Products—Functional Measurement," Volcano Functional Measurement Products US, Mar. 24, 2003, p. 1-2.
Brown et al., "Radiofrequency capacitive heaters: the effect of coupling medium resistivity on power absorption along a mouse leg," Physics in Medicine and Biology, 1993, p. 1-12, vol. 38.
Carrington, "Future of CVI: It's all about plaque: Identification of vulnerable lesions, not 'rusty pipes,' could become cornerstone of preventive cardiology," Diagnostic Imaging, 2001, p. 1-8.
Chen et al., "Percutaneous pulmonary artery denervation completely abolishes experimental pulmonary arterial hypertension in vivo," EuroIntervention, 2013, p. 1-8.
Cimino, "Preventing plaque attack," Mass High Tech, 2001, p. 1-2.
Dahm et al., "Relation of Degree of Laser Debulking of In-Stent Restenosis as a Predictor of Restenosis Rate," The American Journal of Cardiology, 2002, p. 68-70, vol. 90.
De Korte et al., "Characterization of Plaque Components With Intravascular Ultrasound Elastography in Human Femoral and Coronary Arteries In Vitro," Circulation, Aug. 8, 2000, p. 617-623.
Durney et al., "Radiofrequency Radiation Dosimetry Handbook," Oct. 1986, p. 1-2, Fourth Edition.
Durney et al., "Radiofrequency Radiation Dosimetry Handbook: Contents," Oct. 1986, p. 1-5, Fourth Edition.

Fournier-Desseux et al., "Assessment of 1-lead and 2-lead electrode patterns in electrical impedance endotomography," Physiological Measurement, 2005, p. 337-349. Vo. 26, Institute of Physics Publishing.
Fram et al., "Feasibility of Radiofrequency Powered, Thermal Balloon Ablation of Atrioventricular Bypass Tracts via the Coronary Sinus: In Vivo Canine Studies," PACE, Aug. 1995, p. 1518-1530, vol. 18.
Fram et al., "Low Pressure Radiofrequency Balloon Angioplasty: Evaluation in Porcine Peripheral Arteries," JACC, 1993, p. 1512-1521, vol. 21, No. 6, American College of Cardiology.
Fujimori et al., "Significant Prevention of In-Stent Restenosis by Evans Blue in Patients with Acute Myocardial Infarction," American Heart Association, 2002.
Fujita et al., "Sarpogrelate, An Antagonist of 5-HT(2A) Receptor, Treatment Reduces Restenosis After Coronary Stenting," American Heart Association, 2002.
Gabriel, "Appendix A: Experimental Data," 1999, p. 1-21.
Gabriel, "Appendix C: Modeling the frequency dependence of the dielectric properties to a 4 dispersions spectrum," p. 1-49, Nov. 6, 1997.
Gregory et al., "Liquid Core Light Guide for Laser Angioplasty," The Journal of Quantum Electronics, Dec. 1990, p. 2289-2296, vol. 26, No. 12.
Kaplan et al., "Healing after Arterial Dilatation with Radiofrequency Thermal and Nonthermal Balloon Angioplasty Sytems," Journal of Investigative Surgery, 1993, p. 33-52, vol. 6.
Kolata, "New Studies Question Value of Opening Arteries," The New York Times, Mar. 21, 2004, p. 1-5.
Konings et al., "Development of an Intravascular Impedance Catheter for Detection of Fatty Lesions in Arteries," IEEE Transactions on Medical Imaging, Aug. 1997, p. 439-446, vol. 16, No. 4.
Kurtz et al., "Lamellar Refractive Surgery with Scanned Intrastromal Picosecond and Femtosecond Laser Pulses in Animal Eyes," Journal of Refractive Surgery, Sep./Oct. 1998, p. 541-548.
Lee et al., "Thermal Compression and Molding of Atherosclerotic Vascular Tissue With Use of Radiofrequency Energy: Implications for Radiofrequency Balloon Angioplasty," JACC, 1989, p. 1167-1175, vol. 13, No. 5, American College of Cardiology.
Lima et al., "Efficacy and Safety of Oral Sirolimus to Treat and Prevent In-Stent Restenosis: A Pilot Study Results," American Heart Association, 2002, p. 2929.
Lima et al., "Systemic Immunosuppression Inhibits In-Stent Coronary Intimal Proliferation in Renal Transplant Patients," American Heart Association, 2002, p. 2928.
Morice et al., "A Randomized Comparison of a Sirolimus-Eluting Stent With a Standard Stent for Coronary Revascularization," The New England Journal of Medicine, Jun. 6, 2012, p. 1773-1780, vol. 346, No. 23.
Muller-Leisse et al., "Effectiveness and Safety of Ultrasonic Atherosclerotic Plaque Ablation: In Vitro Investigation," CardioVascular and Interventional Radiology, 1993, p. 303-307, vol. 16.
Nair et al., "Regularized Autoregressive Analysis of Intravascular Ultrasound Backscatter: Improvement in Spatial Accuracy of Tissue Maps," IEEE Transactions on Ultrasonics, Apr. 2004, p. 420-431, vol. 51, No. 4.
Popma et al., "Percutaneous Coronary and Valvular Intervention," Braunwald's Heart Disease: A Textbook of Cardiovascular Medicine, 7th edition, p. 1364-1405, 2005.
Resar et al., "Endoluminal Sealing of Vascular Wall Disruptions With Radiofrequency-Heated Balloon Angioplasty," Catheterization and Cardiovascular Diagnosis, 1993, p. 161-167, vol. 29.
Romer et al., "Histopathology of Human Coronary Atherosclerosis by Quantifying Its Chemical Composition With Raman Spectroscopy," Circulation, 1998, p. 878-885, vol. 97.
Schauerte et al., "Catheter Ablation of Cardiac Autonomic Nerves for Prevention of Vagal Atrial Fibrillation," Circulation, 2000, p. 2774-2780, vol. 102.
Scheller et al., "Intracoronary Paclitaxel Added to Contrast Media Inhibits In-Stent Restenosis of Porcine Coronary Arteries," American Heart Association, 2002, p. 2227.

(56) References Cited

OTHER PUBLICATIONS

Scheller et al., "Potential solutions to the current problem: coated balloon," EuroIntervention, 2008, p. C63-C66, vol. 4 (Supplement C).
Shaffer, "Scientific basis of laser energy," Clinics in Sports Medicine, 2002, p. 585-598, vol. 21.
Shmatukha et al., "MRI temperature mapping during thermal balloon angioplasty," Physics in Medicine and Biology, 2006, p. N163-N171, vol. 51.
Slager et al., "Vaporization of Atherosclerotic Plaques by Spark Erosion," J Am Coll Cardiol, 1985, p. 21-25.
Stiles et al., "Simulated Characterization of Atherosclerotic Lesions in the Coronary Arteries by Measurement of Bioimpedance," IEEE Transactions on Biomedical Engineering, Jul. 2003, p. 916-921, vol. 50, No. 7.
Suselbeck et al., "In vivo intravascular electric impedance spectroscopy using a new catheter with integrated microelectrodes," Basic Res Cardiol, 2005, p. 28-34, vol. 100.
Suselbeck et al., "Intravascular electric impedance spectroscopy of atherosclerotic lesions using a new impedance catheter system," Basic Res Cardiol, 2005, p. 446-452, vol. 100.
Tepe et al., "Local Delivery of Paclitaxel to Inhibit Restenosis during Angioplasty of the Leg," The New England Journal of Medicine, 2008, p. 689-699, vol. 358.
"Optical Coherence Tomography: Advantages of OCT," LightLab Imaging Technology, printed Sep. 3, 2003.
"Optical Coherence Tomography: Image Gallery Cardiovascular Procedures," LightLab Imaging Technology, printed Sep. 3, 2003.
"Optical Coherence Tomography: What is OCT?," LightLab Imaging Technology, printed Sep. 3, 2003.
"Optical Coherence Tomography: Why Use OCT?," LightLab Imaging Technology, printed Sep. 3, 2003.
Pieper et al. "Design and implementation of a new computerized system for intraoperative cardiac mapping", J. Appl. Physiol. 71(4): 1529-1539, 1991.
CardioVascular Technologies Inc., "Heated Balloon Device Technology," 11 pages, 2008.
Strategic Business Development, Inc., "Thermal and Disruptive Angioplasty: A Physician's Guide," 8 pages, 1990.
Zhang et al., "Non-contact Radio-Frequency Ablation for Obtaining Deeper Lesions," IEEE Transaction on Biomedical Engineering, vol. 50, No. 2, 6 pages, Feb. 2003.
Lazebnik et al., "Tissue Strain Analytics Virtual Touch Tissue Imaging and Qualification," Siemens Whitepaper, Oct. 2008, 7 pages.
Han et al., "Third-Generation Cryosurgery for Primary and Recurrent Prostate Caner," BJU International, vol. 93, pp. 14-18, 2004.
Zhou et al., "Mechanism Research of Cryoanalgesia," Forefront Publishing Group, 1995.
Florete, "Cryoblative Procedure for Back Pain," Jacksonville Medicine, Oct. 1998, 10 pages.
Stevenson, "Irrigated RF Ablation: Power Titration and Fluid Management for Optimal Safety Efficacy," 2005, 4 pages.
Giliatt et al., "The Cause of Nerve Damage in Acute Compression," Trans Am Neurol Assoc, 1974: 99; 71-4.
Omura et al., "A Mild Acute Compression Induces Neurapraxia in Rat Sciatic Nerve," The International Journal of Neuroscience, vol. 114 (12), pp. 1561-1572, Dec. 2004.
Baun, "Interaction with Soft Tissue," Principles of General & Vascular Sonography, Chapter 2, pp. 23-24, Before Mar. 2012.
Blue Cross Blue Shield Medical Policy, "Surgery Section—MRI-Guided Focused Ultrasound (MRgFUS) for the Treatment of Uterine Fibroids and Other Tumors," 2005, 5 pages.
Gentry et al., "Combines 3D Intracardiac Echo and Ultrasound Ablation," Medical Imaging 2003: Ultrasonic and Signal Processing, vol. 5035, 2003, pp. 166-173.
Lafon et al., "Optmizing the Shape of Ultrasound Transducers for Interstitial Thermal Ablations," MEd Phys. Mar. 2002; 29(3): 290-7 (abstract only).
G. Ter Haar, "Ultrasound Focal Beam Surgery," Ultrasound in Med. & Biol., 1995, vol. 21, No. 9, pp. 1089-1100.
Seip et al., "Transurethral High Intensity Focused Ultrasound: Catheter Based Prototypes and Experimental Results," IEEE Ultrasonics Symposium Proceeding, 2000, 4 pages.
Toytman et al., "Tissue Dissection with Ultrafast Laser Using Extended and Multiple Foci," SPIE Proceeding, Optical Interactions with Tissues and Cells XXI, vol. 7562, 2010, 10 pages.
Zhou et al., "Non-Thermal Ablation of Rabbit Liver VX2 Tumore by Pulsed High Intensity Focused Ultrasound Contrast Agent: Pathological Characteristics," World Journal of Gastroenterology, vol. 14(43), Nov. 21, 2008, pp. 6743-6747.

\* cited by examiner

DEVICES AND METHODS FOR NERVE MODULATION USING LOCALIZED INDIFFERENT ELECTRODES

CROSS-REFERENCE TO RELATED APPLICATIONS

This application claims priority under 35 U.S.C. §119 to U.S. Provisional Application Ser. No. 61/839,243, filed Jun. 25, 2013, the entirety of which is incorporated herein by reference.

FIELD

The invention generally pertains to percutaneous and intravascular devices for nerve modulation and/or ablation.

BACKGROUND

Certain treatments involve, and in some cases require, the temporary or permanent interruption or modification of select nerve function. One example treatment is renal nerve ablation, which can be used to treat conditions related to congestive heart failure. The kidneys produce a sympathetic response to congestive heart failure, which, among other effects, increases the undesired retention of water and/or sodium. Ablating some of the nerves running to the kidneys may reduce or eliminate this sympathetic function, which may provide a corresponding reduction in the associated undesired symptoms.

Many body tissues, such as nerves, including renal nerves, brain tissue, cardiac tissue and the tissue of other body organs, are in close proximity to blood vessels and/or other body cavities. This proximity enables the tissues to be accessed percutaneously or intravascularly through walls of the blood vessels. In some instances, it may be desirable to ablate perivascular nerves using a radio frequency (RF) electrode. In other instances, the perivascular nerves may be ablated by other techniques, including procedures that apply thermal, ultrasonic, laser, microwave, and/or other related energy sources to the vessel wall.

Some treatment devices that are used in procedures involving perivascular nerves, such as renal nerves, employ indifferent electrodes or grounding pads to complete an electric circuit and thereby cause the delivery of electrical current to an RF electrode. In accordance with this technique, a physician carefully identifies an appropriate location of the patient's body, e.g., the patient's legs, on which to place the indifferent electrodes and to create a current path to the RF electrode for completing the circuit. However, using localized indifferent electrodes may result in more efficient modulation/ablation.

It may therefore be beneficial to provide apparatus and methods including, but not limited to, renal nerve modulation systems as well as methods of use and manufacture thereof, that increase and/or otherwise enhance the efficacy of the electrical energy delivered within an intended treatment zone of a patient's body. Additionally or alternatively, it may be beneficial to simplify use of such a device and/or reduce dependency on the patient's anatomy.

SUMMARY

This disclosure provides design, material, manufacturing methods, and use alternatives for medical devices. An example medical device may include a medical device for nerve modulation. The medical device may include an elongate member having a proximal end and a distal end and an inflatable balloon secured adjacent to the distal end of the elongate member. The balloon includes an exterior surface and an interior surface defining a lumen. The balloon may further include at least one section that is permeable to radiofrequency (RF) radiation. The section may extend from the interior surface of the balloon to the exterior surface of the balloon. A first electrode is disposed within the inflatable balloon and indifferent electrodes are disposed external to the inflatable balloon, such as at the exterior surface of the balloon.

An example use of an example medical device may include a method for performing nerve modulation. The method may include providing a nerve modulation system. The nerve modulation system may include an elongate member having a proximal end and a distal end and an inflatable balloon secured adjacent to the distal end of the elongate member. The balloon includes an exterior surface and an interior surface defining a lumen. The balloon may further include at least one section that is permeable to radiofrequency (RF) radiation. The section may extend from the interior surface of the balloon to the exterior surface of the balloon. A first electrode is disposed within the inflatable balloon and indifferent electrodes are disposed external to the inflatable balloon, such as at the exterior surface of the balloon. The nerve modulation system may be advanced through a lumen such that the inflatable balloon is positioned adjacent to a target region. The inflatable balloon may then be expanded with a conductive fluid and RF energy supplied to the first electrode.

The above summary of some embodiments is not intended to describe each disclosed embodiment or every implementation of the present disclosure. The Figures, and Detailed Description, which follow, more particularly exemplify these embodiments.

BRIEF DESCRIPTION OF DRAWINGS

The invention may be more completely understood in consideration of the following detailed description of various embodiments in connection with the accompanying drawings, in which.

Figure 1:
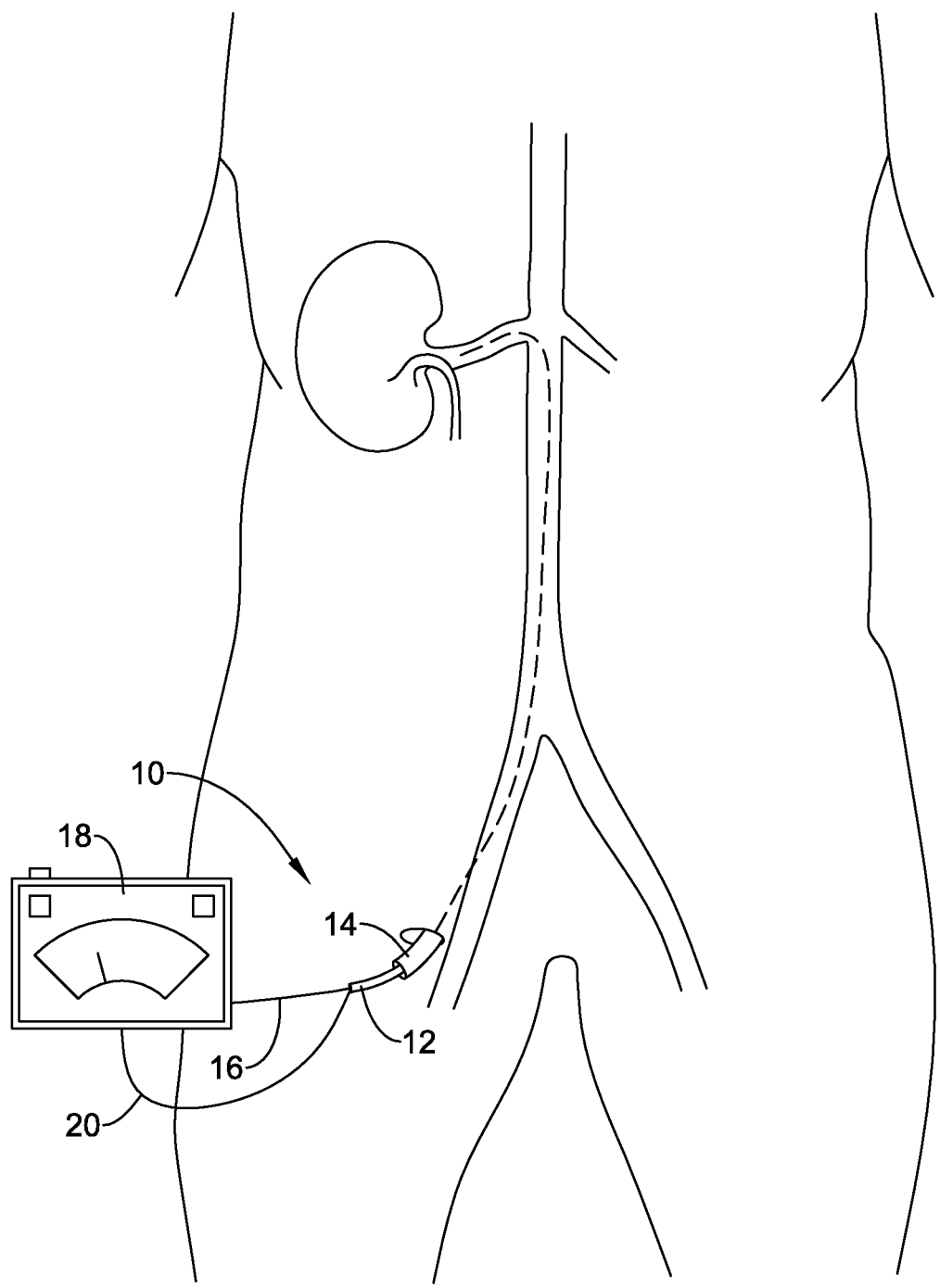
FIG. 1 is a schematic view illustrating a renal nerve modulation system in situ.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

The following description should be read with reference to the drawings, wherein like reference numerals indicate like elements throughout the several views. The drawings, which are not necessarily to scale, are not intended to limit the scope of the claimed invention. The detailed description and drawings illustrate exemplary embodiments of the claimed invention.

All numbers used or otherwise included herein should be considered to be modified by the term "about." The disclosure or recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular indefinite articles "a," "an," and the definite article "the," should be considered to include or otherwise cover both single and plural referents, unless the content clearly dictates otherwise. In other words, these articles are applicable to one or more referents. As used in this specification and the appended claims, the term "or" should be considered to mean "and/or," unless the content clearly dictates otherwise.

References in the specification to "an embodiment," "some embodiments," "other embodiments," etc., indicate that the embodiment described may include a particular feature, structure, or characteristic, but every embodiment may not necessarily include the particular feature, structure, or characteristic. Moreover, such phrases do not necessarily refer to the same embodiment. Further, if a particular feature, structure, or characteristic is described in connection with an embodiment, then it would be within the knowledge of one skilled in the art to affect such feature, structure, or characteristic in connection with, other embodiments, whether or not explicitly described, unless cleared stated to the contrary.

Certain treatments require the temporary or permanent interruption or modification of select nerve function. One example treatment is renal nerve ablation, which is sometimes used to treat conditions related to hypertension, congestive heart failure, diabetes, or other conditions impacted by high blood pressure or salt retention. The kidneys produce a sympathetic response to congestive heart failure, which, among other effects, increases the undesired retention of water and/or sodium. Ablating some of the nerves running to the kidneys may reduce or eliminate this sympathetic function, which may provide a corresponding reduction in the associated undesired symptoms.

Many of the devices and methods are disclosed herein in the context of renal nerve modulation through a blood vessel wall. However, devices and methods of other embodiments may be used in other contexts, such as applications other than where nerve modulation and/or ablation are desired It is contemplated that the devices and methods may be used in other treatment locations and/or applications where nerve modulation and/or other tissue modulation including heating, activation, blocking, disrupting, or ablation are desired, such as, but not limited to: blood vessels, urinary vessels, or in other tissues via trocar and cannula access. For example, the devices and methods described herein can be applied to hyperplastic tissue ablation, cardiac ablation, pulmonary vein isolation, tumor ablation, benign prostatic hyperplasia therapy, nerve excitation or blocking or ablation, modulation of muscle activity, hyperthermia or other warming of tissues, etc. The disclosed methods and apparatus can be applied to any relevant medical procedure, involving both human and non-human subjects. The term modulation refers to ablation and other techniques that may alter the function of affected nerves and other tissue. In some embodiments, a single ablation device may be used to sequentially perform multiple ablations, if desirable.

FIG. 1 is a schematic view of an illustrative renal nerve modulation system in situ. The renal nerve modulation system 10 may include one or more conductive element(s) 16 for providing power to a renal nerve modulation device. An illustrative renal nerve modulation device may include an intravascular catheter or nerve modulation device 12 optionally disposed within a delivery sheath or guide catheter 14. The delivery sheath 14 may be adapted to slidably contain the intravascular catheter 12 if a radially expanding distal portion (not shown) of the intravascular catheter 12 is in a non-expanded configuration, as will be discussed in more detail below. A distal end of each of the conductive element(s) 16 is attached to one or more electrodes at a location at or near a distal end of the intravascular catheter 12. A proximal end of each of the conductive element(s) 16 may be connected to a power and control unit 18, which supplies electrical energy used to activate the one or more electrodes. The power and control unit 18 is typically located outside of the patient's body. The electrodes are capable of modulating or ablating tissue upon being suitably activated via the control unit 18.

In the following disclosure, the terms electrode and electrodes may be considered to be equivalent to elements capable of ablating adjacent tissue. The disclosure of "adjacent tissue" is intended to cover any tissue located sufficiently proximate the electrode(s) for ablation, and the locations and distances involved are intended to vary depending on application and/or other factors. The delivery sheath 14, elongate member and conductive element(s) 16 can be formed of any currently known, related art, and/or later developed materials that enable ablation of adjacent tissue. In some embodiments, these materials may include internal and/or external layers of lubricious material(s).

The power and control unit 18 may include monitoring elements to monitor parameters, such as power, temperature, voltage, pulse size, impedance and/or shape, and/or other suitable parameters. The power and control unit 18 may also include, or otherwise be used with, sensors mounted along the renal nerve modulation device, as well as suitable controls for performing the desired procedure. In some embodiments, the control unit 18 may control a radio frequency (RF) electrode. The electrode may be configured to operate at a frequency of approximately 460 kHz. However, any desired frequency in the RF range may be used, for example, from 450-500 kHz. In addition, other types of ablation devices may be used as desired including, but not limited to, devices that involve resistance heating, ultrasound, microwave, and laser technologies. The power and control unit 18 may supply different forms of power to these devices. In some embodiments, the renal nerve modulation device 12 may include indifferent electrodes coupled to the power and control unit 18, via a conductive element 20, and placed locally with or otherwise proximate to the RF electrodes to complete the circuit. These indifferent electrodes are discussed in detail with reference to subsequent figures.

Figure 2:
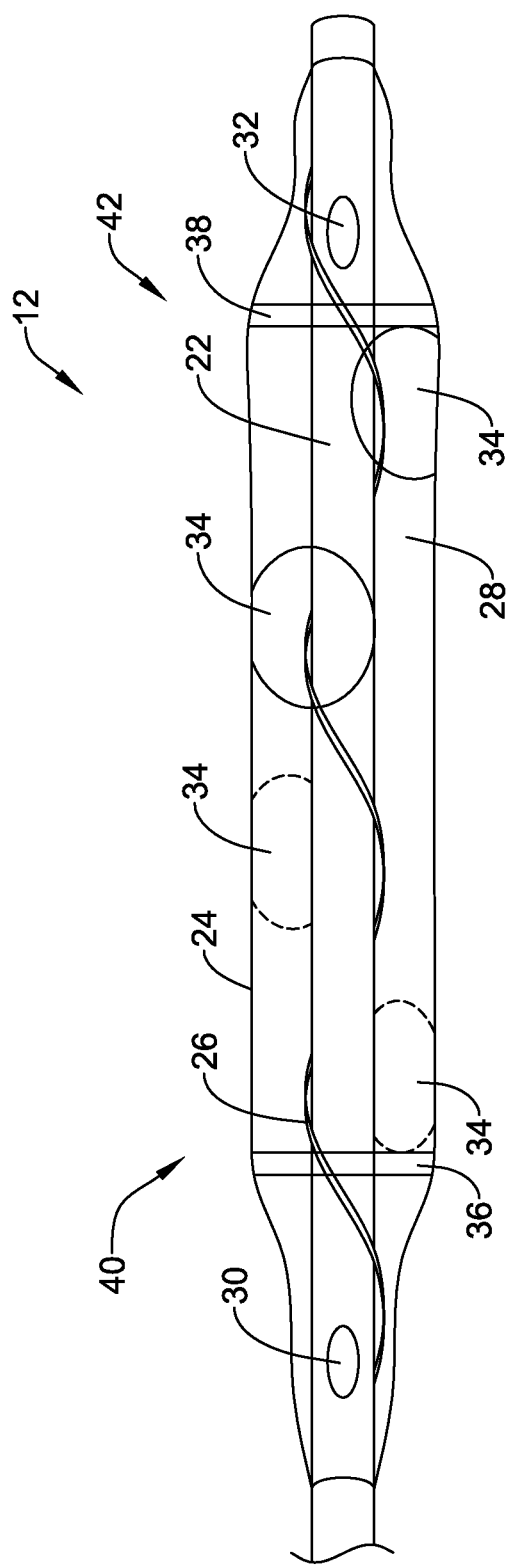
FIG. 2 illustrates a distal portion of an illustrative renal nerve modulation device.

FIG. 2 illustrates a distal portion of an illustrative renal nerve modulation device 12, which includes localized indifferent electrodes according to a first embodiment of the present disclosure. The distal portion of the renal nerve modulation device 12 includes an elongate shaft or member 22, an inflatable balloon 24, and an electrode 26. The elongate member 22 has a distal end that extends proximally to a proximal end that is configured to remain outside of the patient's body. The proximal end of the elongate member 22 may be located adjacent to the power and control unit 18 although this is not required, and may include a hub (not shown). The hub can be used for connecting other diagnostic and/or treatment devices by providing a port for a guidewire, an inflation lumen, a return lumen, etc. The elongate member 22 may have a long, thin, flexible tubular configuration. However, one of ordinary skill in the art will appreciate other suitable configurations, including but not limited to the following shapes: rectangle, oval, irregular, etc. In addition, the elongate member 22 may have a cross-sectional configuration adapted to be received in a desired vessel, such as a renal artery. For example, the elongate member 22 may be sized and configured to accommodate passage through the intravascular path, which leads from a percutaneous access site in, for example, the femoral, brachial, or radial artery, to a targeted treatment site, such as within a renal artery.

The elongate member 22 may include one or more lumens, such as, but not limited to, a guidewire lumen, a fluid lumen connected to a fluid inlet port 32 and/or a fluid lumen connected to a fluid outlet port 30. In some embodiments, the fluid lumens can be connected to a system to circulate the fluid through the balloon 24 or to a system that supplies new fluid and collects the evacuated fluid. It can be appreciated that embodiments may function with merely a single fluid inlet lumen and a single fluid outlet into the balloon. It can also be appreciated that other lumen configurations are contemplated. For example, the guidewire lumen and fluid lumens may be disposed within each other or may be concentric. The guidewire lumen may be the innermost lumen and may be surrounded by the fluid inlet lumen which, in turn may be surrounded by the fluid outlet lumen. In another contemplated embodiment, only one of the fluid inlet and fluid outlet lumens is disposed around the guidewire lumen and the other of the fluid inlet and fluid outlet lumens extends parallel to and spaced apart from the guidewire lumen. Another contemplated embodiment lacks the fluid outlet lumen and the fluid inlet lumen is disposed around or concentrically around the guidewire lumen. In another contemplated embodiment, the guidewire lumen is omitted and the system includes only the fluid inlet lumen or only the fluid inlet and outlet lumens. In another illustrative embodiment, the fluid inlet lumen, fluid outlet lumen, and guidewire lumen may extend side-by-side.

The inflatable balloon 24 is positioned adjacent to the distal end of the elongate member 22, and secured to encompass the fluid inlet 32 and the fluid outlet 30 of the elongate member 22. When in use, the balloon 24 is preferably filled with a conductive fluid 28 such as saline to allow the ablation energy to be transmitted from the electrode 26 through windows 34 that are permeable to RF radiation. Other appropriate conductive fluids include hypertonic solutions, contrast solution and mixtures of saline or hypertonic saline solutions with contrast solutions. The conductive fluid may be introduced through a fluid inlet 32 and evacuated through a fluid outlet 30, both in elongate member 22. While not explicitly shown, one or more sensors, such as thermocouple, may be included and may be disposed on the elongate member 22, on the balloon 24 or at another suitable location.

The balloon 24 may be formed having a first inner layer and a second outer layer. A window 34 may be formed in the balloon 24 by the absence of the second layer. The first layer is preferably made from an RF permeable material. One suitable material is a hydrophilic polyurethane. Other suitable materials include other hydrophilic polymers such as hydrophilic Pebax, hydrophilic nylons, hydrophilic polyesters, or block co-w polymers with built-in hydrophilic blocks. Hydrophilic Pebax grades that may be suitable include Pebax MV1074, Pebax MV 1041, Pebax MP 1878, Pebax MV-3000, and Pebax MH-1657. In some embodiments, one or more of the hydrophilic polymers such as the hydrophilic Pebax grades are used in blends with other polymers used in balloons such as Pebax 6333, Pebax 7033, Pebax 7233, Nylon 12, Vestamid L2101F, Grilamid L20, and Grilamid L25. Suitable hydrophilic polymers may exhibit between 6% to 120% hydrophilicity (or % water absorption), between 20% to 50% hydrophilicity or other suitable range. The second layer is preferably made from an electrically non-conductive polymer such as a non-hydrophilic polyurethane, Pebax, nylon, polyester or block-copolymer. Other suitable materials include any of a range of electrically non-conductive polymers. The materials of the first layer and the second layer may be selected to have good bonding characteristics between the two layers. For example, a balloon 24 may be formed from a first layer made from a hydrophilic Pebax and a second layer made from a regular or non-hydrophilic Pebax. In other embodiments, a suitable tie layer (not illustrated) may be provided between the two layers.

The balloon 24 includes an interior surface defining a lumen. Windows 34 may extend from the interior surface to the exterior surface of the inflatable balloon 24. The windows 34 may be arranged to achieve complete or substantially complete circumferential coverage of the blood vessel, while being spaced apart longitudinally. Embodiments are intended to include any suitable number and/or shape of windows 34. For example, some embodiments include 1, 2, 3, 4, 5, 6, 7, 8, 9, 10 or more windows 34. These windows 34 can be defined in any suitable shape, including but not limited to the following shapes: circle, oval, rectangle, or polygon. Moreover, windows 34 that have a different length and width may be oriented so that the largest dimension is parallel to the longitudinal axis, perpendicular to the longitudinal axis, or at any other angle with respect to the longitudinal axis, such as at a forty-five degree angle. In some embodiments, windows 34 may have an aspect ratio of 2:1, 3:1 or 4:1, where the major dimension is perpendicular to the longitudinal axis of the inflatable balloon 24. In some embodiments, the windows 34 may have a customized pattern so as to provide a particular treatment pattern.

Some embodiments include an RF electrode 26, while other embodiments use other types of conductive elements, to supply power to the windows 34. The RF electrode 26, or other conductive element, may extend along the outer surface of the elongate member 22, or may be embedded within the elongate member 22. The electrode 26 proximal to the balloon 24 is preferably electrically insulated and is used to transmit power to the portion of the electrode 26 disposed in the balloon 24. The electrode 26 may be formed of platinum, gold, stainless steel, cobalt alloys, and/or any other non-oxidizing material. In some embodiments, titanium, tantalum, and/or tungsten may be used. The electrode 26 may extend along substantially the entire length of the balloon 24, or alternatively may extend only as far as the distal edge of the most distal window 34. The electrode 26 may have a generally helical shape, and may be wrapped around the elongate member 22. In some embodiments, the electrode 26 may be bonded to the elongate member 22. The electrode 26 and windows 34 may be arranged so that the electrode 26 extends directly under the windows 34.

In some embodiments, the electrode 26 may be a wire, ribbon, or may be a tubular member disposed around the elongate member 22. Some embodiments may include a plurality of electrodes, where each of the electrodes may be fixed to the elongate member 22 under an individual window 34. Each of these electrodes may share a common connection to the conductive element 16. In other embodiments that include more than one electrode 26, each electrode 26 may be separately controllable. In such embodiments, the balloon 24 may be partitioned into more than one chamber, and each chamber may include one or more electrodes. The electrode 26 may be selected to provide a particular level of flexibility to the inflatable balloon 24 to enhance the maneuverability of the system 10. However, other embodiments include numerous other types of variations of the electrode(s) 26.

The intravascular catheter 12 may further include one or more indifferent electrodes that are in communication with the body of the patient to complete the circuit. In some embodiments, the indifferent electrodes are configured as expandable bands 36, 38. These expandable bands 36, 38 may be positioned around the outer circumference of the inflatable balloon 24. A first expandable band 36 may be positioned adjacent to a proximal end region 40 of the inflatable balloon 24 and a second expandable band 38 may be positioned adjacent to a distal end region 42 of the inflatable balloon 24. The expandable bands 36, 38 may be secured to an outer surface of the balloon 24. In some instances, expansion of the balloon 24 will result in expansion of the expandable bands 36, 38. In other embodiments, expansion of the bands 36, 38 may be controlled independently of the balloon 24. The indifferent, or ground, electrodes, (for example, expandable bands 36, 38) may be connected to power and control unit 18 through a conductive element 20 (as shown in FIG. 1). It is contemplated that each expandable band 36, 38 may be connected to the power and control unit 18 through separate electrical conductors or through the same electrical conductor.

The expandable bands 36, 38, may be formed of any suitable currently known, related art, and/or later developed biocompatible conductive material, such as but are not limited to, polymers, metals, and/or alloys. While FIG. 2 illustrates two expandable bands 36, 38, it is contemplated that there may be any number of indifferent electrodes desired, such as, but not limited to, one, two, three, four, or more. The number of indifferent electrodes may be selected based on the desired treatment. For example, in some instances a greater number of active and/or indifferent electrodes may result in more efficient procedure. When the indifferent electrodes act solely as ground electrodes, altering the number and/or size of the electrodes may alter the way energy is dispersed which may help direct the formation of lesions in a more controlled manner. It is further contemplated that the expandable bands 36, 38 may be placed at any longitudinal location along the balloon 24 and/or elongate shaft 22 desired to achieve the desired current distribution. However, the expandable bands 36, 38 should not be placed in contact with the active windows 34 as this may provide a direct return path for the electrical current. In some instances, the expandable bands 36, 38 may extend around the entire circumference of the balloon 24 while in other instances, the expandable bands 36, 38 may extend around only a portion of the circumference.

Further, while expandable bands 36, 38 have been described as indifferent or ground electrodes, where lesions are not formed adjacent to the bands 36, 38, it is contemplated that the expandable bands 36, 38 and the windows 34 may be operated in a bi-polar mode, such that lesions can be formed adjacent the windows 34 and the expandable bands 36, 38.

During a modulation procedure, the renal nerve modulation device 12 may be advanced through the vasculature until the balloon 24 is positioned adjacent to a desired treatment region. The balloon 24 may then be expanded using a conductive fluid 28 such that the balloon 24 contacts the vessel wall or is in close proximity to the vessel wall. Electrical current may then be supplied to electrode 26 through conductive element 16. Ablation energy may be conducted through conductive fluid 28 to windows 34 that are permeable to RF energy. The RF energy may travel through the tissue between the windows 34, or active electrodes, and the expandable bands 36, 38, or indifferent electrodes. It is contemplated that the control and power unit 18 may control the intensity of the electrical current to achieve the desired lesion size. For example, lesions may be formed in the range of from 1 millimeter (mm) to 6 mm from the active electrode. As the outer layer of the balloon 24 is formed from a non-conductive material, the expandable bands 36, 38 may be electrically insulated from the windows 34 effectively preventing current from traveling directly through the balloon 24 from the windows 34 to the expandable bands 36, 38. It is contemplated that the expandable bands 36, 38 should be placed within conductive pathway contact, e.g. the vessel wall, or sometimes blood. Once the procedure is finished at a particular location, the inflatable balloon 24 may be partially or entirely deflated, and the elongate member 22 may be moved to a different location, such as the other renal artery. The procedure may then be repeated at another location as desired using conventional, related art and/or later developed delivery techniques, such as by and repositioning the localized indifferent electrodes and windows 34 of the inflatable balloon 24.

Placement of the indifferent electrode(s) in close proximity to the active electrode(s) may reduce inefficiencies involved with using external ground pads. For example, with localized indifferent electrodes, the RF field and efficacy may be more contained and confined than with external ground pads. This may reduce unforeseen peripheral complications, for example, but not limited to: grounding pad burns, poor conduction, excessive ablation, thrombus events, etc. It is further contemplated that local grounding of the RF signal may prevent peripheral loss of RF energy and may also reduce the occurrence of high impedance.

Figure 3:
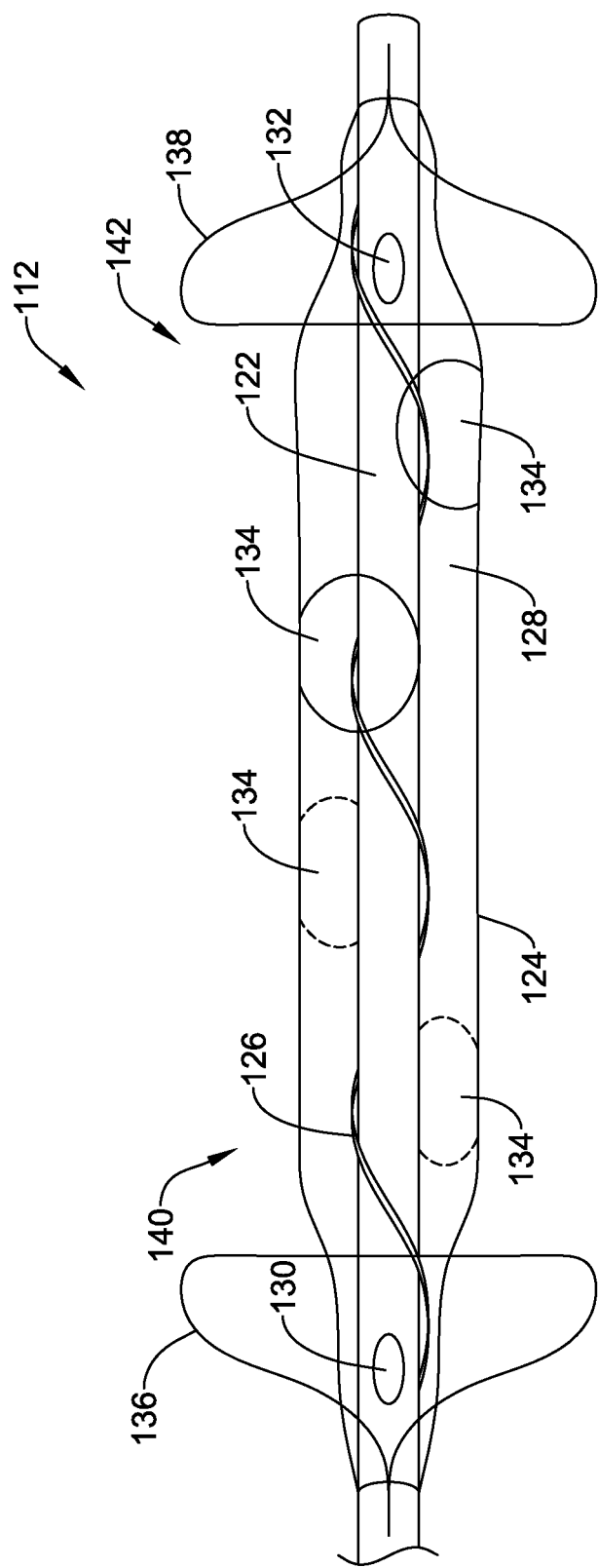
FIG. 3 illustrates a distal portion of another illustrative renal nerve modulation device.

FIG. 3 illustrates a distal portion of another illustrative renal nerve modulation device 112. Nerve modulation device 112 may be similar in form and function to nerve modulation device 12 described above. Modulation device 112 may include an elongate shaft 122, an expandable member or balloon 124 coupled to the shaft 122, and an electrode 126 disposed within balloon 124. In some embodiments, the balloon 124 may further include one or more sensors (not explicitly shown), such as but not limited to, temperature sensors, for monitoring the modulation procedure. When in use, the balloon 124 can be filled with a conductive fluid 128 such as saline to allow the ablation energy (e.g. radiofrequency energy) to be transmitted from electrode 126 through the conductive fluid, to one or more windows 134 disposed along balloon 124. It is contemplated that while balloon 124 is not illustrated as having two layers, balloon 124 may be formed in similar manner to balloon 24 described above to form virtual windows 134. Accordingly, windows 134 may absorb fluid (e.g., the conductive fluid) so that energy exposed to the conductive fluid can be conducted to windows 134 such that windows 134 are capable of ablating tissue.

Electrode 126 (or a conductive element to supply power to electrode 126) may extend along the elongate shaft 122 may be embedded within the shaft. Electrode 126 proximal to the balloon may be electrically insulated and may be used to transmit power to the portion of the electrode 126 disposed within balloon 124. Electrode 126 may be similar in form and function to electrode 26 discussed above.

Electrode 126 may extend along substantially the whole length of the balloon 124 or may extend only as far as the distal edge of the most distal virtual window 134. The electrode 126 may have a generally helical shape and may be wrapped around elongate shaft 122, although this is not required. The electrode 126 and windows 134 may be arranged so that the electrode 126 extends directly under the windows 134. It can be appreciated that there are many variations contemplated for electrode 126 such as, but not limited to, those discussed above.

Electrode 126 may be activated by supplying energy to electrode 126. The energy may be supplied at 400-500 KHz at about 5-30 watts of power. These are just examples, other energies are contemplated. The energy may be transmitted through the medium of the conductive fluid and through windows 134 to the blood vessel wall to modulate or ablate the tissue. A second non-conductive layer of the balloon prevents the energy transmission through the balloon wall except at windows 134 (which lack second layer) similar to balloon 24 discussed above.

FIG. 3 illustrates four windows 134, spaced about the balloon 124. The windows 134 of the embodiment shown in FIG. 3 may be generally oblong in shape. However, any number or shape of windows 134 can be provided to perform the disclosed operation(s). In other words, embodiments are intended to include any number of windows 134 and/or shape of the windows 134. For example, some embodiments include 1, 2, 3, 4, 5, 6, 7, 8, 9, 10 or more virtual electrodes, and include virtual electrodes that are circular, oval, rectangular, polygonal, and/or any other shape to perform the disclosed operation(s). Moreover, windows 134 having different lengths and widths may be oriented so that the largest dimension is parallel to the longitudinal axis, perpendicular to the longitudinal axis, and/or at another angle with respect to the longitudinal axis, such as a 45 degree angle. In some embodiments, the virtual electrode(s) 228 may have a custom pattern to provide a particular treatment pattern.

The elongate shaft 122 may be a generally long and elongated, flexible tubular construction that may be inserted into the body for a medical diagnosis and/or treatment. The elongate shaft 122 may include a proximal and a distal end, and extend proximally from its distal end to the proximal end that is configured to remain outside of a patient's body. Elongate shaft 122 may include one or more lumens for providing an inflation fluid to the balloon 124, a guidewire lumen, auxiliary lumen, etc. It is contemplated that the lumens may be arranged in any manner desired. Inflation fluid 128 may be delivered through a fluid inlet port 132 and evacuated through a fluid outlet port 130.

The nerve modulation device 112 may further include one or more indifferent electrodes that are in communication with the body of the patient to complete the circuit. In some embodiments, the indifferent electrodes are configured as expandable hoops 136, 138. These expandable hoops 136, 138 may have first collapsed position (not explicitly shown) and a second expanded position. In the expanded position, the expandable hoops 136, 138 may expand and extend around a circumference of the balloon 124. In other embodiments, the expandable hoops 136, 138 may not extend around the circumference of the balloon 124; rather they may be positioned to expand away from the elongate shaft 122 or balloon 124. The expandable hoops 136, 138 may be secured either to the elongate shaft 122 or the balloon 124, as desired.

A first expandable hoop 136 may be positioned adjacent to a proximal end region 140 of the inflatable balloon 124 and a second expandable hoop 138 may be positioned adjacent to a distal end region 142 of the inflatable balloon 124. In some instances, expansion of the balloon 124 will result in expansion of the expandable hoops 136, 138. In other embodiments, expansion of the hoops 136, 138 may be controlled independently of the balloon 124, for example using a user actuated through a mechanism such as a pull wire or self expanding material. Independent expansion of the hoops 136, 138 may allow the hoops 136, 138 to be expanded to conform to the shape of the vessel or to a custom position. The indifferent, or ground, electrodes, (for example, expandable hoops 136, 138) may be connected to a power and control unit, such as power and control unit 18 shown in FIG. 1, through an electrical conductor (not explicitly shown). It is contemplated that each expandable hoop 136, 138 may be connected to the power and control unit through separate electrical conductors or through the same electrical conductor.

Figure 5:
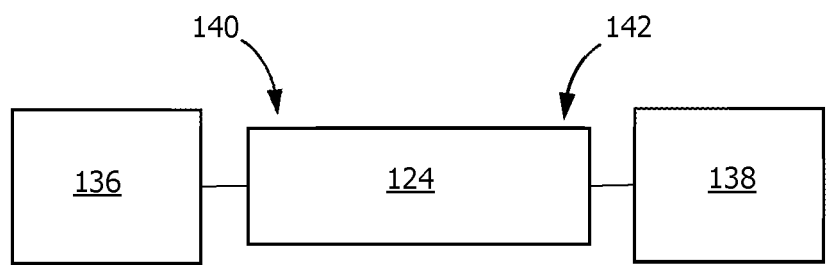
FIG. 5 is a schematic block diagram illustrating the relative positions of a first expandable hoop, an inflatable balloon and second expandable hoop at a distal portion of another illustrative renal nerve modulation device.

In a variation of the positioning of the first expandable hoop 136, inflatable balloon 124 and second expandable hoop 138 of FIG. 3, a schematic block diagram is presented in FIG. 5 illustrating an embodiment wherein a first expandable hoop 136 is positioned proximal to a proximal end 140 of an inflatable balloon 124 and a second expandable hoop 138 is positioned distal to a distal end 142 of the inflatable balloon 124.

The expandable hoops 136, 138, may be formed of any suitable currently known, related art, and/or later developed biocompatible conductive material, such as but are not limited to, polymers, metals, and/or alloys. While FIG. 3 illustrates two expandable hoops 136, 138, it is contemplated that there may be any number of indifferent electrodes desired, such as, but not limited to, one, two, three, four, or more. The number of indifferent electrodes may be selected based on the desired treatment. For example, in some instances a greater number of active and/or indifferent electrodes may result in more efficient procedure. When the indifferent electrodes act solely as ground electrodes, altering the number and/or size of the electrodes may alter the way energy is dispersed which may help direct the formation of lesions in a more controlled manner. It is further contemplated that the expandable hoops 136, 138 may be placed at any longitudinal location along the balloon 124 and/or elongate shaft 122 desired to achieve the desired current distribution. However, the expandable hoops 136, 138 should not be placed in contact with the active windows 134 as this may provide a direct return path for the electrical current. Further, while expandable hoops 136, 138 have been described as indifferent or ground electrodes, where lesions are not formed adjacent to the hoops 136, 138, it is contemplated that the expandable hoops 136, 138 and the windows 134 may be operated in a bi-polar mode, such that lesions can be formed adjacent the windows 134 and the expandable hoops 136, 138.

During a modulation procedure, the renal nerve modulation device 112 may be advanced through the vasculature until the balloon 124 is positioned adjacent to a desired treatment region. The balloon 124 may then be expanded using a conductive fluid 128 such that the balloon 124 contacts the vessel wall or is in close proximity to the vessel wall. Electrical current may then be supplied to electrode 126 through an electrical conductor. Ablation energy may be conducted through conductive fluid 128 to windows 134 that are permeable to RF energy. The RF energy may travel through the tissue between the windows 134, or active electrodes, and the expandable hoops 136, 138, or indifferent electrodes. It is contemplated that the control and power unit may control the intensity of the electrical current to achieve the desired lesion size. For example, lesions may be formed in the range of from 1 millimeter (mm) to 6 mm from the active electrode. As the outer layer of the balloon 124 is formed from a non-conductive material, the expandable hoops 136, 138 may be electrically insulated from the windows 134 effectively preventing current from traveling directly through the balloon 124 from the windows 134 to the expandable hoops 136, 138. It is contemplated that the expandable hoops 136, 138 should be placed within conductive pathway contact, e.g. the vessel wall, or sometimes blood. Once the procedure is finished at a particular location, the inflatable balloon 124 may be partially or entirely deflated, and the elongate shaft or member 122 may be moved to a different location, such as the other renal artery. The procedure may then be repeated at another location as desired using conventional, related art and/or later developed delivery techniques, such as by repositioning the localized indifferent electrodes and windows 134 of the inflatable balloon 124.

Placement of the indifferent electrode(s) in close proximity to the active electrode(s) may reduce inefficiencies involved with using external ground pads. For example, with localized indifferent electrodes, the RF field and efficacy may be more contained and confined than with external ground pads. This may reduce unforeseen peripheral complications, for example, but not limited to: grounding pad burns, poor conduction, excessive ablation, thrombus events, etc. It is further contemplated that local grounding of the RF signal may prevent peripheral loss of RF energy and may also reduce the occurrence of high impedance.

Figure 4:
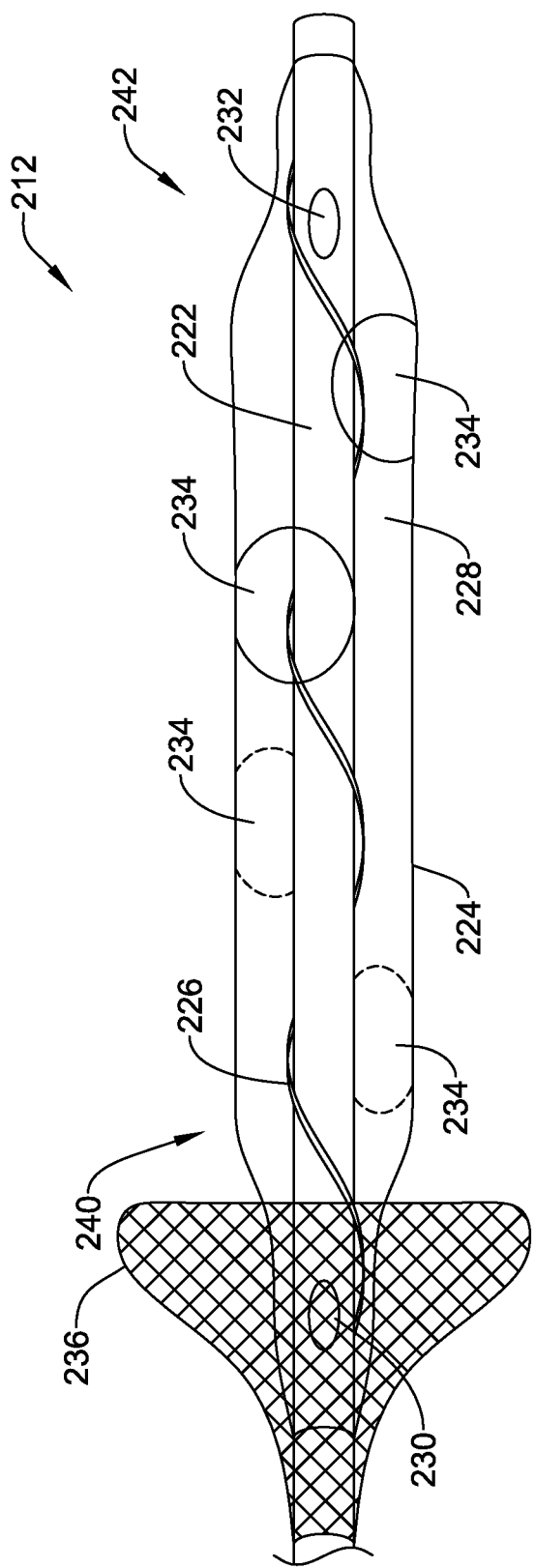
FIG. 4 illustrates a distal portion of another illustrative renal nerve modulation device.

FIG. 4 illustrates a distal portion of another illustrative renal nerve modulation device 212. Nerve modulation device 212 may be similar in form and function to nerve modulation devices 12, 112 described above. Modulation device 212 may include an elongate shaft 222, an expandable member or balloon 224 coupled to the shaft 222, and an electrode 226 disposed within balloon 224. In some embodiments, the balloon 224 may further include one or more sensors (not explicitly shown), such as but not limited to, temperature sensors, for monitoring the modulation procedure. When in use, the balloon 224 can be filled with a conductive fluid 228 such as saline to allow the ablation energy (e.g. radiofrequency energy) to be transmitted from electrode 226 through the conductive fluid, to one or more windows 234 disposed along balloon 224. It is contemplated that while balloon 224 is not illustrated as having two layers, balloon 224 may be formed in similar manner to balloon 24 described above to form virtual windows 234. Accordingly, windows 234 may absorb fluid (e.g., the conductive fluid) so that energy exposed to the conductive fluid can be conducted to windows 234 such that windows 234 are capable of ablating tissue.

Electrode 226 (or a conductive element to supply power to electrode 226) may extend along the elongate shaft 222 may be embedded within the shaft. Electrode 226 proximal to the balloon may be electrically insulated and may be used to transmit power to the portion of the electrode 226 disposed within balloon 224. Electrode 226 may be similar in form and function to electrodes 26, 126 discussed above. Electrode 226 may extend along substantially the whole length of the balloon 224 or may extend only as far as the distal edge of the most distal virtual window 234. The electrode 226 may have a generally helical shape and may be wrapped around elongate shaft 222, although this is not required. The electrode 226 and windows 234 may be arranged so that the electrode 226 extends directly under the windows 234. It can be appreciated that there are many variations contemplated for electrode 226 such as, but not limited to, those discussed above.

Electrode 226 may be activated by supplying energy to electrode 226. The energy may be supplied at 400-500 KHz at about 5-30 watts of power. These are just examples, other energies are contemplated. The energy may be transmitted through the medium of the conductive fluid and through windows 234 to the blood vessel wall to modulate or ablate the tissue. A second non-conductive layer of the balloon prevents the energy transmission through the balloon wall except at windows 234 (which lack second layer) similar to balloon 24 discussed above.

FIG. 4 illustrates four windows 234, spaced about the balloon 224. The windows 234 of the embodiment shown in FIG. 4 may be generally oblong in shape. However, any number or shape of windows 234 can be provided to perform the disclosed operation(s). In other words, embodiments are intended to include any number of windows 234 and/or shape of the windows 234. For example, some embodiments include 1, 2, 3, 4, 5, 6, 7, 8, 9, 10 or more virtual electrodes, and include virtual electrodes that are circular, oval, rectangular, polygonal, and/or any other shape to perform the disclosed operation(s). Moreover, windows 234 having different lengths and widths may be oriented so that the largest dimension is parallel to the longitudinal axis, perpendicular to the longitudinal axis, and/or at another angle with respect to the longitudinal axis, such as a 45 degree angle. In some embodiments, the virtual electrode(s) 228 may have a custom pattern to provide a particular treatment pattern.

The elongate shaft 222 may be a generally long and elongated, flexible tubular construction that may be inserted into the body for a medical diagnosis and/or treatment. The elongate shaft 222 may include a proximal and a distal end, and extend proximally from its distal end to the proximal end that is configured to remain outside of a patient's body. Elongate shaft 222 may include one or more lumens for providing an inflation fluid to the balloon 224, a guidewire lumen, auxiliary lumen, etc. It is contemplated that the lumens may be arranged in any manner desired. Inflation fluid 228 may be delivered through a fluid inlet port 232 and evacuated through a fluid outlet port 230.

The nerve modulation device 212 may further include one or more indifferent electrodes that are in communication with the body of the patient to complete the circuit. In some embodiments, the indifferent electrode is configured as an expandable basket 236. The expandable basket 236 may have first collapsed position (not explicitly shown) and a second expanded position. In the expanded position, the expandable basket 236 may expand and extend around a circumference of the balloon 224. In other embodiments, the expandable basket 236 may not extend around the circumference of the balloon 224; rather it may be positioned to expand away from the elongate shaft 222 or balloon 224. The expandable basket 236 may be secured either to the elongate shaft 222 or the balloon 224, as desired.

A first expandable basket 236 may be positioned adjacent to a proximal end region 240 of the inflatable balloon 224. However, it is contemplated that the expandable hoop basket may be positioned adjacent to a distal end region 242 of the inflatable balloon 224. In some instances, expansion of the balloon 224 will result in expansion of the expandable basket 236. In other embodiments, expansion of the basket 236 may be controlled independently of the balloon 224, for example user actuated through a mechanism such as a pull wire or self expanding material. Independent expansion of the basket 236 may allow the basket 236 to be expanded to conform to the shape of the vessel or to a custom position.

The indifferent, or ground, electrodes, (for example, expandable basket 236) may be connected to a power and control unit, such as power and control unit 18 shown in FIG. 1, through an electrical conductor (not explicitly shown). It is contemplated that each expandable basket 236 may be connected to the power and control unit through separate electrical conductors or through the same electrical conductor.

The expandable basket 236, may be formed of any suitable currently known, related art, and/or later developed biocompatible conductive material, such as but are not limited to, polymers, metals, and/or alloys. The basket 236 may be formed in a number of different manners, for example, the basket 236 may be formed of one or more filaments, braided, wound, or woven to form a basket structure. In other embodiments, the basket 236 may have a stent-like structure and may be braided, woven, or cut from a tube. While FIG. 4 illustrates a single expandable basket 236, it is contemplated that there may be any number of indifferent electrodes desired, such as, but not limited to, two, three, four, or more. The number of indifferent electrodes may be selected based on the desired treatment. For example, in some instances a greater number of active and/or indifferent electrodes may result in more efficient procedure. When the indifferent electrodes act solely as ground electrodes, altering the number and/or size of the electrodes may alter the way energy is dispersed which may help direct the formation of lesions in a more controlled manner. It is further contemplated that the expandable basket 236 may be placed at any longitudinal location along the balloon 224 and/or elongate shaft 222 desired to achieve the desired current distribution. However, the expandable basket 236 should not be placed in contact with the active windows 234 as this may provide a direct return path for the electrical current.

Further, while expandable basket 236 has been described as an indifferent or ground electrode, where lesions are not formed adjacent to the basket 236, it is contemplated that the expandable basket 236 and the windows 234 may be operated in a bi-polar mode, such that lesions can be formed adjacent the windows 234 and the expandable basket 236.

During a modulation procedure, the renal nerve modulation device 212 may be advanced through the vasculature until the balloon 224 is positioned adjacent to a desired treatment region. The balloon 224 may then be expanded using a conductive fluid 228 such that the balloon 224 contacts the vessel wall or is in close proximity to the vessel wall. Electrical current may then be supplied to electrode 226 through an electrical conductor. Ablation energy may be conducted through conductive fluid 228 to windows 234 that are permeable to RF energy. The RF energy may travel through the tissue between the windows 234, or active electrodes, and the expandable basket 236, or indifferent electrode. It is contemplated that the control and power unit may control the intensity of the electrical current to achieve the desired lesion size. For example, lesions may be formed in the range of from 1 millimeter (mm) to 6 mm from the active electrode. As the outer layer of the balloon 224 is formed from a non-conductive material, the expandable basket 236 may be electrically insulated from the windows 234 effectively preventing current from traveling directly through the balloon 224 from the windows 234 to the expandable basket 236. It is contemplated that the expandable basket 236 should be placed within conductive pathway contact, e.g. the vessel wall, or sometimes blood. Once the procedure is finished at a particular location, the inflatable balloon 224 may be partially or entirely deflated, and the elongate shaft or member 222 may be moved to a different location, such as the other renal artery. The procedure may then be repeated at another location as desired using conventional, related art and/or later developed delivery techniques, such as by repositioning the localized indifferent electrodes and windows 234 of the inflatable balloon 224.

Placement of the indifferent electrode(s) in close proximity to the active electrode(s) may reduce inefficiencies involved with using external ground pads. For example, with localized indifferent electrodes, the RF field and efficacy may be more contained and confined than with external ground pads. This may reduce unforeseen peripheral complications, for example, but not limited to: grounding pad burns, poor conduction, excessive ablation, thrombus events, etc. It is further contemplated that local grounding of the RF signal may prevent peripheral loss of RF energy and may also reduce the occurrence of high impedance.

Although the embodiments described above are disclosed in the context of renal nerve modulation devices, those skilled in the art will understand that the principles disclosed above can be applied to other types of devices and can be implemented in different ways without departing from the scope of the invention as defined by the claims. In particular, constructional details, including manufacturing techniques and materials, are well within the understanding of those of ordinary skill in the art and have not been disclosed in detail herein. These and other modifications and variations are well within the scope of the present disclosure and can be envisioned and implemented by those of ordinary skill in the art.

Moreover, while specific embodiments may have been illustrated and described collectively herein, it should be appreciated that any subsequent arrangement designed to achieve the same or similar purpose may be substituted for the specific embodiments described and shown herein. This disclosure is intended to cover any and all subsequent adaptations or variations of the various embodiments. Combinations of the above embodiments, and other embodiments not specifically described herein, will be apparent to those of ordinary skill in the art upon reviewing the present disclosure.

Other embodiments of the present disclosure will be apparent to those skilled in the art from consideration of the specification and practice of the embodiments disclosed herein. It is intended that the specification and examples be considered as exemplary only, and departure in form and detail may be made without departing from the scope and spirit of the present disclosure as defined by the following claims.

What is claimed is:
1. An intravascular catheter, comprising:
an elongate member having a proximal end and a distal end;
an inflatable balloon secured to the elongate member adjacent to the distal end thereof, the inflatable balloon further including an interior surface, an exterior surface, a lumen defined by the interior surface and comprising at least one section that is permeable to radiofrequency (RF) radiation, the at least one section extending from the interior surface of the inflatable balloon to the exterior surface of the inflatable balloon;
a first electrode disposed within the inflatable balloon; and
first and second indifferent electrodes disposed adjacent and external to the inflatable balloon, wherein the first indifferent electrode comprises a first expandable hoop positioned proximal to a proximal end of the inflatable balloon and the second indifferent electrode comprises a second expandable hoop positioned distal to a distal end of the inflatable balloon.

2. An intravascular catheter, comprising:
an elongate member having a proximal end and a distal end;
an inflatable balloon secured to the elongate member adjacent to the distal end thereof, the inflatable balloon further including an interior surface an exterior surface a lumen defined by the interior surface and comprising at least one section that is permeable to radiofrequency (RF) radiation, the at least one section extending from the interior surface of the inflatable balloon to the exterior surface of the inflatable balloon;
a first electrode disposed within the inflatable balloon; and
first and second expandable indifferent electrodes disposed external to the inflatable balloon, the first expandable indifferent electrode positioned adjacent a proximal end of the inflatable balloon and the second expandable indifferent electrode positioned adjacent a distal end of the inflatable balloon,
wherein the first and second expandable indifferent electrodes comprise first and second expandable hoops, and wherein each of the first and second expandable hoops is self-expanding.

3. An intravascular catheter, comprising:
an elongate member having a proximal end and a distal end;
an inflatable balloon secured to the elongate member adjacent to the distal end thereof, the inflatable balloon further including an interior surface, an exterior surface, a lumen defined by the interior surface and comprising at least one section that is permeable to radiofrequency (RF) radiation, the at least one section extending from the interior surface of the inflatable balloon to the exterior surface of the inflatable balloon;
a first electrode disposed within the inflatable balloon; and
first and second expandable indifferent electrodes disposed external to the inflatable balloon, the first expandable indifferent electrode positioned adjacent a proximal end of the inflatable balloon and the second expandable indifferent electrode positioned adjacent a distal end of the inflatable balloon,
wherein the first and second expandable indifferent electrodes are configured to be expanded independently of expansion of the inflatable balloon.

4. The intravascular catheter of claim 3, wherein the first expandable indifferent electrode is positioned proximal to the proximal end of the inflatable balloon and the second expandable indifferent electrode is positioned distal to the distal end of the inflatable balloon.

* * * * *